(12) United States Patent
Cabannes

(10) Patent No.: US 11,293,049 B2
(45) Date of Patent: Apr. 5, 2022

(54) MODULATION OF ACCESSIBILITY OF HOST NUCLEIC ACIDS TO NUCLEIC ACID DIGESTING ENZYMES IN ACELLULAR BIOLOGICAL FLUIDS

(71) Applicant: PATHOQUEST, Paris (FR)

(72) Inventor: Éric Cabannes, Antony (FR)

(73) Assignee: PATHOQUEST, Paris (FR)

( * ) Notice: Subject to any disclaimer, the term of this patent is extended or adjusted under 35 U.S.C. 154(b) by 24 days.

(21) Appl. No.: 16/068,457

(22) PCT Filed: Jan. 6, 2017

(86) PCT No.: PCT/EP2017/050251
§ 371 (c)(1),
(2) Date: Jul. 6, 2018

(87) PCT Pub. No.: WO2017/118719
PCT Pub. Date: Jul. 13, 2017

(65) Prior Publication Data
US 2019/0002958 A1    Jan. 3, 2019

Related U.S. Application Data

(60) Provisional application No. 62/276,650, filed on Jan. 8, 2016.

(30) Foreign Application Priority Data

Jan. 8, 2016  (EP) .................................... 16150594

(51) Int. Cl.
*C12Q 1/6806* (2018.01)
*C12N 15/10* (2006.01)

(52) U.S. Cl.
CPC ....... *C12Q 1/6806* (2013.01); *C12N 15/1003* (2013.01)

(58) Field of Classification Search
CPC .............. C12N 15/1003; C12Q 1/6806; C12Q 2527/125
See application file for complete search history.

(56) References Cited

U.S. PATENT DOCUMENTS

| | | | |
|---|---|---|---|
| 9,944,974 B2 | 4/2018 | Tarendeau | |
| 2004/0072193 A1* | 4/2004 | Mitsuhashi | ........ C12N 15/1017 435/6.16 |
| 2015/0337362 A1* | 11/2015 | Tarendeau | ......... C12N 15/1003 435/5 |

FOREIGN PATENT DOCUMENTS

| | | | |
|---|---|---|---|
| WO | 2009/015484 A1 | 2/2009 | |
| WO | 2010/062354 A1 | 6/2010 | |
| WO | WO-2013045457 A1 * | 4/2013 | ........... C12Q 1/6806 |
| WO | 2014/114896 A1 | 7/2014 | |
| WO | 2015/062699 A1 | 5/2015 | |
| WO | 2016/169579 A1 | 10/2016 | |

OTHER PUBLICATIONS

DeJong et al., "Quantitation of Varicella-Zoster Virus DNA in Whole Blood, Plasma, and Serum by PCR and Electrochemiluminescence," Journal of Clinical Microbiology, July, vol. 38, No. 7, pp. 2568-2573. (Year: 2000).*
International Search Report, dated Mar. 24, 2017, from corresponding PCT/EP2017/050251 application.

* cited by examiner

*Primary Examiner* — Young J Kim
(74) *Attorney, Agent, or Firm* — Nixon & Vanderhye

(57) ABSTRACT

Disclosed is a method for isolating, amplifying, and sequencing infectious agents' nucleic acids from an acellular fraction of a biological fluid using detergents and nucleic acids-digesting enzymes. Also disclosed is a kit-of-parts including detergents and nucleic acids-digesting enzymes for the implementation of the methods described.

10 Claims, No Drawings
Specification includes a Sequence Listing.

SEQUENCE LISTING

```
<160> NUMBER OF SEQ ID NOS: 13

<210> SEQ ID NO 1
<211> LENGTH: 35
<212> TYPE: DNA
<213> ORGANISM: Artificial Sequence
<220> FEATURE:
<223> OTHER INFORMATION: /note="Primer-K8"
      /note="K is T or G"

<400> SEQUENCE: 1
gtgagtgatg gttgaggtag tgtggagkkk kkkkk                          35

<210> SEQ ID NO 2
<211> LENGTH: 27
<212> TYPE: DNA
<213> ORGANISM: Artificial Sequence
<220> FEATURE:
<223> OTHER INFORMATION: fixed sequence

<400> SEQUENCE: 2
gtgagtgatg gttgaggtag tgtggag                                   27

<210> SEQ ID NO 3
<211> LENGTH: 36
<212> TYPE: DNA
<213> ORGANISM: Artificial Sequence
<220> FEATURE:
<223> OTHER INFORMATION: /note="Primer-K9"
      /note="K is T or G"

<400> SEQUENCE: 3
gtgagtgatg gttgaggtag tgtggagkkk kkkkkk                         36

<210> SEQ ID NO 4
<211> LENGTH: 37
<212> TYPE: DNA
<213> ORGANISM: Artificial Sequence
<220> FEATURE:
<223> OTHER INFORMATION: /note="Primer-K10"
      /note="K is T or G"

<400> SEQUENCE: 4
```
gtgagtgatg gttgaggtag tgtggagkkk kkkkkkk                    37

<210> SEQ ID NO 5
<211> LENGTH: 34
<212> TYPE: DNA
<213> ORGANISM: Artificial Sequence
<220> FEATURE:
<223> OTHER INFORMATION: /note="Primer-K7"
      /note="K is T or G"

<400> SEQUENCE: 5
gtgagtgatg gttgaggtag tgtggagkkk kkkk                      34

<210> SEQ ID NO 6
<211> LENGTH: 33
<212> TYPE: DNA
<213> ORGANISM: Artificial Sequence
<220> FEATURE:
<223> OTHER INFORMATION: /note="Primer-K6"
      /note="K is T or G"

<400> SEQUENCE: 6
gtgagtgatg gttgaggtag tgtggagkkk kkk                       33

<210> SEQ ID NO 7
<211> LENGTH: 32
<212> TYPE: DNA
<213> ORGANISM: Artificial Sequence
<220> FEATURE:
<223> OTHER INFORMATION: /note="Primer-K5"
      /note="K is T or G"

<400> SEQUENCE: 7
gtgagtgatg gttgaggtag tgtggagkkk kk                        32

<210> SEQ ID NO 8
<211> LENGTH: 35
<212> TYPE: DNA
<213> ORGANISM: Artificial Sequence
<220> FEATURE:
<223> OTHER INFORMATION: /note="Primer-Y8"
      /note="Y is T or C"

<400> SEQUENCE: 8
ctcactcatc cttcacctac tctccacyyy yyyyy                     35

<210> SEQ ID NO 9
<211> LENGTH: 36
<212> TYPE: DNA
<213> ORGANISM: Artificial Sequence
<220> FEATURE:
<223> OTHER INFORMATION: /note="Primer-Y9"
      /note="Y is T or C"

<400> SEQUENCE: 9
ctcactcatc cttcacctac tctccacyyy yyyyyy                    36

<210> SEQ ID NO 10
<211> LENGTH: 37
<212> TYPE: DNA
<213> ORGANISM: Artificial Sequence
<220> FEATURE:
<223> OTHER INFORMATION: /note="Primer-Y10"
      /note="Y is T or C"

<400> SEQUENCE: 10
ctcactcatc cttcacctac tctccacyyy yyyyyyy                   37

```
<210> SEQ ID NO 11
<211> LENGTH: 34
<212> TYPE: DNA
<213> ORGANISM: Artificial Sequence
<220> FEATURE:
<223> OTHER INFORMATION: /note="Primer-Y7"
      /note="Y is T or C"

<400> SEQUENCE: 11
ctcactcatc cttcacctac tctccacyyy yyyy                            34

<210> SEQ ID NO 12
<211> LENGTH: 33
<212> TYPE: DNA
<213> ORGANISM: Artificial Sequence
<220> FEATURE:
<223> OTHER INFORMATION: /note="Primer-Y6"
      /note="Y is T or C"

<400> SEQUENCE: 12
ctcactcatc cttcacctac tctccacyyy yyy                             33

<210> SEQ ID NO 13
<211> LENGTH: 32
<212> TYPE: DNA
<213> ORGANISM: Artificial Sequence
<220> FEATURE:
<223> OTHER INFORMATION: /note="Primer-Y5"
      /note="Y is T or C"

<400> SEQUENCE: 13
ctcactcatc cttcacctac tctccacyyy yy                              32
```

MODULATION OF ACCESSIBILITY OF HOST NUCLEIC ACIDS TO NUCLEIC ACID DIGESTING ENZYMES IN ACELLULAR BIOLOGICAL FLUIDS

FIELD OF INVENTION

The present invention relates to a method for modulating the accessibility of host nucleic acids (HNA) in an acellular fraction of a biological fluid. The present invention further relates to a method for detecting infectious agents in an acellular fraction of a biological fluid.

BACKGROUND OF INVENTION

The detection of pathogenic infectious agents in biological fluids should be performed in the shortest possible time, in particular in the case of septicemia, for which the mortality remains high in spite of the broad range of antibiotics which are available to doctors.

The level of infectious agents in a patient's body fluid is generally very low compared to host components from the subject. Typical biological samples like plasma, serum, cerebrospinal fluid devoid of living or dead cells discarded by centrifugation still contains high amounts of cell free HNA. In a particular case, circulating free cells (not associated with other cells), such as host cells, or fetal cells in a case of pregnancy, can release HNA.

Methods to decrease the amount of host nucleic acids are described in WO2010/062354 and WO2014/114896 and consist in treating biological fluids containing cells with detergent for disrupting the cellular membranes and then treating the resulting sample with nucleases (enzymes having DNase and/or RNase activity). However, these approaches have been of partial efficacy as it remains HNA that is resistant to nucleases in the treated sample.

The Applicant surprisingly demonstrates here that incubation of an acellular fraction of a biological fluid with detergent and nucleases improves the detection of infectious agents in a sample. As a result, the Applicant provides a new method for strongly decreasing the concentration of HNA in an acellular fraction of a biological sample, which results in a better detection of infectious agents in said sample.

SUMMARY

The present invention relates to an in vitro method for isolating, amplifying, and sequencing infectious agents' nucleic acids from an acellular fraction of a biological fluid.

In one embodiment, the method comprises contacting the acellular fraction of a biological fluid with at least one detergent and at least one nucleic acids-digesting enzyme.

In one embodiment, the method further comprises the extraction and sequencing of the infectious agents' nucleic acids.

In one embodiment, the method according to the invention comprises the steps of:
 a) contacting the acellular fraction of a biological fluid with at least one detergent and at least one nucleic acids-digesting enzyme,
 b) extracting infectious agents' nucleic acids,
 c) optionally, reverse-transcribing infectious agents' genomic RNAs,
 d) amplifying infectious agents' genomic DNA and/or infectious agents' cDNA, and
 e) sequencing amplified infectious agents' genomic DNA and/or infectious agents' cDNA.

In one embodiment, the sequencing of the infectious agents' nucleic acids is carried out by Next Generation Sequencing (NGS).

In one embodiment, the infectious agent is selected from the group comprising viruses, bacteria, fungi, protozoans, and parasites.

In one embodiment, the at least one detergent is selected from the group comprising non-ionic detergent, zwitterionic detergent, and anionic detergent.

In one embodiment, the at least one detergent is a non-ionic detergent.

In one embodiment, the at least one detergent is selected from the group comprising saponin, Triton, NP-40, Tween and derivative detergents thereof.

In one embodiment, the at least one detergent is saponin.

In one embodiment, the at least one detergent is sapogenin with a sapogenin content of about 5% to about 50%.

In one embodiment, the at least one nucleic acids-digesting enzyme is a nuclease having DNase and/or RNase activity.

In one embodiment, the at least one nucleic acids-digesting enzyme is selected from the group comprising baseline-zero DNase, benzonase, DNase I, DNase II, endonuclease III, endonuclease IV, endonuclease V, endonuclease VIII, exonuclease I, exonuclease III, exonuclease V, exonuclease VII, exonuclease VIII, exonuclease T, lambda exonuclease, micrococcal nuclease, mung bean nuclease, nuclease BAL-31, nuclease P1, nuclease S1, T4 endonuclease V, T5 exonuclease, T7 endonuclease I, and T7 exonuclease.

In one embodiment, the presence of residual cells within the fraction does not affect the accessibility or the enrichment of the infectious agent in the fraction.

The present invention also relates to a kit-of-parts.

In one embodiment, the kit-of-parts for carrying out the methods according to the present invention.

In one embodiment, the kit-of-parts comprises:
 a) at least one detergent,
 b) at least one nucleic acids-digesting enzyme.

In one embodiment, the kit-of-parts comprises:
 a) at least one detergent, selected from the group comprising saponin, Triton, NP-40, Tween or a derivative thereof,
 b) at least one nucleic acids-digesting enzyme, selected from the group comprising baseline-zero DNase, benzonase, DNase I, DNase II, endonuclease III, endonuclease IV, endonuclease V, endonuclease VIII, exonuclease I, exonuclease III, exonuclease V, exonuclease VII, exonuclease VIII, exonuclease T, lambda exonuclease, micrococcal nuclease, mung bean nuclease, nuclease BAL-31, nuclease P1, nuclease S1, T4 endonuclease V, T5 exonuclease, T7 endonuclease I, and T7 exonuclease.

In one embodiment, the kit-of-parts may comprise reagents. In one embodiment, the kit-of-parts may comprise instructions for use in a method according to the present invention.

Thus, in one embodiment, the kit-of-parts comprises:
 a) at least one detergent, selected from the group comprising saponin, Triton, NP-40, Tween or a derivative thereof,
 b) at least one nucleic acids-digesting enzyme, selected from the group comprising baseline-zero DNase, benzonase, DNase I, DNase II, endonuclease III, endonuclease IV, endonuclease V, endonuclease VIII, exonuclease I, exonuclease III, exonuclease V, exonuclease VII, exonuclease VIII, exonuclease T, lambda exonuclease, micrococcal nuclease, mung bean nuclease, nuclease BAL-31, nuclease P1, nuclease S1, T4 endonuclease V, T5 exonuclease, T7 endonuclease I, and T7 exonuclease, c) optionally, reagents, and d) optionally, instructions for use in a method according to the present invention.

In one embodiment, the reagents are selected from the group comprising nucleic acid extraction reagents, reverse transcription reagents, nucleic acid amplification reagents, nucleic acid clean-up reagents, nucleic acid size-selection reagents, nucleic acid quantification reagents, nucleic acid library preparation reagents, nucleic acid library sequencing reagents, and internal controls.

In one embodiment, the reagents comprise nucleic acid extraction reagents, reverse transcriptase, vent exo-DNA polymerase, dNTPs, oligonucleotide primers with sequence set forth as any of SEQ ID NO: 1 or 3-13, oligonucleotide primers with sequence set forth as SEQ ID NO: 2, exonuclease I and/or SPRI beads.

Definitions

In the present invention, the following terms have the following meanings:

"Acellular fraction" refers to a biological fluid depleted in about 90%, 91%, 92%, 93%, 94%, 95%, 96%, 97%, 98%, preferably 99%, more preferably 100% of its cellular content. The acellular fraction of a biological fluid may be obtained by any well-known technique in the art. For example, in one embodiment where the biological fluid is blood, said acellular fraction may be obtained from a centrifugation step from about 100 to about 500 g for about 5 minutes to about 20 minutes, preferably at 300 g for 10 minutes.

"Host nucleic acids" or "HNA" refer to nucleic acids issued from a subject.

"Modulating" refers to an improvement or increase in the accessibility of HNA.

"Primer" refers to an oligonucleotide that is capable of hybridizing or annealing with a nucleic acid and serving as an initiation site for nucleotide polymerization under appropriate conditions, such as the presence of nucleoside triphosphates and an enzyme for polymerization, such as DNA or RNA polymerase or reverse transcriptase, in an appropriate buffer and at a suitable temperature.

"Amplification" refers to the process of producing multiple copies, i.e., at least 2 copies, of a desired template sequence. Techniques to amplify nucleic acids are well known to the skilled artisan, and include specific amplification methods as well as random amplification methods.

"Reverse transcription" refers to the replication of RNA using a RNA-directed DNA polymerase (reverse transcriptase, RT) to produce complementary strands of DNA (cDNA). The reverse-transcription of RNAs may be carried out by techniques well known to the skilled artisan, using a reverse transcriptase enzyme and a mix of 4 deoxyribonucleotides triphosphate (dNTPs), namely deoxyadenosine triphosphate (dATP), deoxycytidine triphosphate (dCTP), deoxyguanosine triphosphate (dGTP) and (deoxy)thymidine triphosphate (dTTP).

"Subject" refers to any species such as for example domestic animals (i.e., farm fish, pets, ruminants, pigs, horses), wide-life animals and human. In one embodiment, a subject may be a "patient", i.e., a mammal or more preferably a human, who/which is awaiting the receipt of, or is receiving medical care or was/is/will be the object of a medical procedure, or is monitored for the development of a disease.

"Internal control" refers to one or more materials used in an assay as a point of reference and/or comparison in order to make judgements as to the presence, absence or level of one or more factors being analyzed. Some internal control may comprise negative or positive control samples. Negative controls are samples known to lack one or more factors being analyzed. Positive controls are samples known to comprise one or more factors being analyzed. In one embodiment, the internal control can be an internal control nucleic acid sequence that is added in the sample at a given time point or at given time points, at a known concentration. In one embodiment, the internal control can be a virus such as a bacteriophage that is added in the sample at a given time point or at given time points, at a known concentration.

"About" preceding a figure means plus or less 10% of the value of said figure.

DETAILED DESCRIPTION

One object of the invention is an in vitro method for enriching an infectious agent in an acellular fraction of a biological fluid comprising contacting the acellular fraction of a biological fluid with at least one detergent and at least one nucleic acids-digesting enzyme.

Another object of the invention is a method for modulating the accessibility of host nucleic acids (HNA) to nucleic acids-digesting enzymes in an acellular fraction of a biological fluid comprising contacting the acellular fraction of a biological fluid with at least one detergent and at least one nucleic acids-digesting enzyme.

Another object of the invention is an in vitro method for increasing the ratio of the nucleic acids of infectious agents to the total nucleic acids in an acellular fraction of a biological fluid comprising contacting the acellular fraction of a biological fluid with at least one detergent and at least one nucleic acids-digesting enzyme.

Another object of the invention is an in vitro method for isolating, amplifying, and sequencing viral nucleic acids from an acellular fraction of a biological fluid comprising contacting the acellular fraction of a biological fluid with at least one detergent and at least one nucleic acids-digesting enzyme.

Another object of the invention is an in vitro method for isolating, amplifying, and sequencing bacterial nucleic acids from an acellular fraction of a biological fluid comprising contacting the acellular fraction of a biological fluid with at least one detergent and at least one nucleic acids-digesting enzyme.

In one embodiment of the invention, the structure or the entirety of the infectious agent is not affected by the methods of the invention.

In one embodiment, the in vitro method for enriching an infectious agent in an acellular fraction of a biological fluid comprises contacting the acellular fraction of a biological fluid with at least one detergent and at least one nucleic acids-digesting enzyme.

In one embodiment, the in vitro method for enriching an infectious agent in an acellular fraction of a biological fluid comprises contacting the acellular fraction of a biological fluid with at least one detergent and at least one nucleic acids-digesting enzyme, extracting infectious agents' nucleic acids and sequencing said extracted infectious agents' nucleic acids.

In one embodiment, the method for modulating the accessibility of host nucleic acids (HNA) to nucleic acids-digesting enzymes in an acellular fraction of a biological fluid comprises contacting the acellular fraction of a biological fluid with at least one detergent and at least one nucleic acids-digesting enzyme.

In one embodiment, the method for modulating the accessibility of host nucleic acids (HNA) to nucleic acids-digesting enzymes in an acellular fraction of a biological fluid comprises contacting the acellular fraction of a biological fluid with at least one detergent and at least one nucleic acids-digesting enzyme, extracting infectious agents' nucleic acids and sequencing said extracted infectious agents' nucleic acids.

In one embodiment, the in vitro method for increasing the ratio of the nucleic acids of infectious agents to the total nucleic acids in an acellular fraction of a biological fluid comprises contacting the acellular fraction of a biological fluid with at least one detergent and at least one nucleic acids-digesting enzyme.

In one embodiment, the in vitro method for increasing the ratio of the nucleic acids of infectious agents to the total nucleic acids in an acellular fraction of a biological fluid comprises contacting the acellular fraction of a biological fluid with at least one detergent and at least one nucleic acids-digesting enzyme, extracting infectious agents' nucleic acids and sequencing said extracted infectious agents' nucleic acids.

In one embodiment, the in vitro method for isolating, amplifying, and sequencing infectious agents' nucleic acids from an acellular fraction of a biological fluid comprises contacting the acellular fraction of a biological fluid with at least one detergent and at least one nucleic acids-digesting enzyme.

In one embodiment, the in vitro method for isolating, amplifying, and sequencing infectious agents' nucleic acids from an acellular fraction of a biological fluid comprises contacting the acellular fraction of a biological fluid with at least one detergent and at least one nucleic acids-digesting enzyme, extracting infectious agents' nucleic acids and sequencing said extracted infectious agents' nucleic acids.

In one embodiment, the in vitro method for isolating, amplifying, and sequencing infectious agents' nucleic acids from an acellular fraction of a biological fluid comprises:
a) contacting the acellular fraction of a biological fluid with at least one detergent and at least one nucleic acids-digesting enzyme,
b) extracting infectious agents' nucleic acids,
c) optionally, reverse-transcribing infectious agents' genomic RNAs,
d) amplifying infectious agents' genomic DNA and/or infectious agents' cDNA,
e) sequencing amplified infectious agents' genomic DNA and/or infectious agents' cDNA.

In one embodiment, sequencing of the amplified infectious agents' genomic DNA and/or infectious agents' cDNA is carried out by random sequencing by high throughput sequencing (HTS) or next generation sequencing (NGS). Thus, in one embodiment, the method further comprises steps of infectious agents' genomic DNA and/or infectious agents' cDNA library construction, including but not limited to, DNA cleaning, DNA sizing, and/or DNA library preparation.

In one embodiment, the in vitro method for isolating, amplifying, and sequencing viral nucleic acids from an acellular fraction of a biological fluid comprises contacting the acellular fraction of a biological fluid with at least one detergent and at least one nucleic acids-digesting enzyme, extracting viral nucleic acids and sequencing said extracted viral nucleic acids.

In one embodiment, the method further comprises a step of viral RNA reverse transcription. In one embodiment, the method further comprises a step of viral DNA and/or viral cDNA amplification. In one embodiment, the method further comprises a step of nucleic acid cleaning. In one embodiment, the method further comprises a step of nucleic acid sizing. In one embodiment, the method further comprises a step of nucleic acid quantification. In one embodiment, the method further comprises a step of nucleic acid library preparation.

In one embodiment, the in vitro method for isolating, amplifying, and sequencing viral nucleic acids from an acellular fraction of a biological fluid comprises:
a) contacting the acellular fraction of a biological fluid with at least one detergent and at least one nucleic acids-digesting enzyme,
b) extracting viral nucleic acids,
c) optionally, reverse-transcribing viral genomic RNAs,
d) amplifying viral genomic DNA and/or viral cDNA,
e) sequencing amplified viral genomic DNA and/or viral cDNA.

In one embodiment, sequencing of the amplified viral genomic DNA and/or cDNA is carried out by random sequencing by high throughput sequencing (HTS) or next generation sequencing (NGS). Thus, in one embodiment, the method further comprises steps of viral genomic DNA and/or cDNA library construction, including but not limited to, DNA cleaning, DNA sizing, and/or DNA library preparation.

In one embodiment, the in vitro method for isolating, amplifying, and sequencing bacterial nucleic acids from an acellular fraction of a biological fluid comprises contacting the acellular fraction of a biological fluid with at least one detergent and at least one nucleic acids-digesting enzyme.

In one embodiment, the in vitro method for isolating, amplifying, and sequencing bacterial nucleic acids from an acellular fraction of a biological fluid comprises selectively lysing the non-bacterial cells in a cellular fraction of a biological fluid to retrieve an acellular fraction of said biological fluid, contacting the acellular fraction of a biological fluid with at least one detergent and at least one nucleic acids-digesting enzyme.

In one embodiment, the method further comprises a step of bacterial DNA amplification. In one embodiment, the method further comprises a step of nucleic acid cleaning. In one embodiment, the method further comprises a step of nucleic acid sizing. In one embodiment, the method further comprises a step of nucleic acid quantification. In one embodiment, the method further comprises a step of nucleic acid library preparation.

In one embodiment, the in vitro method for isolating, amplifying, and sequencing bacterial nucleic acids from an acellular fraction of a biological fluid comprises pelleting bacteria from said acellular fraction of a biological fluid, contacting the pellet with at least one detergent and at least one nucleic acids-digesting enzyme, extracting bacterial nucleic acids and sequencing said extracted bacterial nucleic acids.

In one embodiment, the in vitro method for isolating, amplifying, and sequencing bacterial nucleic acids from an acellular fraction of a biological fluid comprises selectively lysing the non-bacterial cells in a cellular fraction of a biological fluid to retrieve an acellular fraction of said biological fluid, contacting the acellular fraction of a biological fluid with at least one detergent and at least one nucleic acids-digesting enzyme, extracting bacterial nucleic acids and sequencing said extracted bacterial nucleic acids.

In one embodiment, the in vitro method for isolating, amplifying, and sequencing bacterial nucleic acids from an acellular fraction of a biological fluid comprises:
 a) pelleting bacteria from the acellular fraction of a biological fluid,
 b) contacting the pellet from the acellular fraction of a biological fluid with at least one detergent and at least one nucleic acids-digesting enzyme,
 c) extracting bacterial genomic DNA,
 d) amplifying bacterial genomic DNA,
 e) sequencing amplified bacterial genomic DNA.

In one embodiment, the in vitro method for isolating, amplifying, and sequencing bacterial nucleic acids from an acellular fraction of a biological fluid comprises:
 a) selectively lysing the non-bacterial cells in a cellular fraction of a biological fluid to retrieve an acellular fraction of said biological fluid,
 b) contacting said acellular fraction of a biological fluid with at least one detergent and at least one nucleic acids-digesting enzyme,
 c) extracting bacterial genomic DNA,
 d) amplifying bacterial genomic DNA,
 e) sequencing amplified bacterial genomic DNA.

In one embodiment, sequencing of the amplified bacterial genomic DNA is carried out by random sequencing by high throughput sequencing (HTS) or next generation sequencing (NGS). Thus, in one embodiment, the method further comprises steps of bacterial genomic DNA library construction, including but not limited to, DNA cleaning, DNA sizing, and/or DNA library preparation.

In one embodiment, the in vitro method for isolating, amplifying, and sequencing fungal nucleic acids from an acellular fraction of a biological fluid comprises contacting the acellular fraction of a biological fluid with at least one detergent and at least one nucleic acids-digesting enzyme.

In one embodiment, the in vitro method for isolating, amplifying, and sequencing fungal nucleic acids from an acellular fraction of a biological fluid comprises selectively lysing the non-fungal cells in a cellular fraction of a biological fluid to retrieve an acellular fraction of said biological fluid, contacting the acellular fraction of a biological fluid with at least one detergent and at least one nucleic acids-digesting enzyme.

In one embodiment, the method further comprises a step of fungal DNA amplification. In one embodiment, the method further comprises a step of nucleic acid cleaning. In one embodiment, the method further comprises a step of nucleic acid sizing. In one embodiment, the method further comprises a step of nucleic acid quantification. In one embodiment, the method further comprises a step of nucleic acid library preparation.

In one embodiment, the in vitro method for isolating, amplifying, and sequencing fungal nucleic acids from an acellular fraction of a biological fluid comprises pelleting fungi from said acellular fraction of a biological fluid, contacting the pellet with at least one detergent and at least one nucleic acids-digesting enzyme, extracting fungal nucleic acids and sequencing said extracted fungal nucleic acids.

In one embodiment, the in vitro method for isolating, amplifying, and sequencing fungal nucleic acids from an acellular fraction of a biological fluid comprises selectively lysing the non-fungal cells in a cellular fraction of a biological fluid to retrieve an acellular fraction of said biological fluid, contacting the acellular fraction of a biological fluid with at least one detergent and at least one nucleic acids-digesting enzyme, extracting fungal nucleic acids and sequencing said extracted fungal nucleic acids.

In one embodiment, the in vitro method for isolating, amplifying, and sequencing fungal nucleic acids from an acellular fraction of a biological fluid comprises:
 a) pelleting fungi from the acellular fraction of a biological fluid,
 b) contacting the pellet from the acellular fraction of a biological fluid with at least one detergent and at least one nucleic acids-digesting enzyme,
 c) extracting fungal genomic DNA,
 d) amplifying fungal genomic DNA,
 e) sequencing amplified fungal genomic DNA.

In one embodiment, the in vitro method for isolating, amplifying, and sequencing fungal nucleic acids from an acellular fraction of a biological fluid comprises:
 a) selectively lysing the non-fungal cells in a cellular fraction of a biological fluid to retrieve an acellular fraction of said biological fluid,
 b) contacting said acellular fraction of a biological fluid with at least one detergent and at least one nucleic acids-digesting enzyme,
 c) extracting fungal genomic DNA,
 d) amplifying fungal genomic DNA,
 e) sequencing amplified fungal genomic DNA.

In one embodiment, sequencing of the amplified bacterial genomic DNA is carried out by random sequencing by high throughput sequencing (HTS) or next generation sequencing (NGS). Thus, in one embodiment, the method further comprises steps of fungal genomic DNA library construction, including but not limited to, DNA cleaning, DNA sizing, and/or DNA library preparation.

The acellular fraction of a biological fluid in the meaning of the present invention refers to a fraction of a biological fluid comprising less than about 10%, 9%, 8%, 7%, 6%, 5%, 4%, 3%, 2%, 1% of the cellular material present originally in the biological fluid.

In one embodiment, said acellular fraction can be obtained from a biological fluid having already undergone steps to discard cells from a biological fluid.

In one embodiment, said acellular fraction can be obtained from a biological fluid having already undergone steps to lyse cells from a biological fluid.

In another embodiment, said acellular fraction comprises residual cells that do not affect the enrichment or the accessibility of the infectious agent.

According to the invention, examples of biological fluids include but are not limited to, blood, amniotic fluid, aqueous humor, bile, bladder lavage, breast exudate, bronchio-alveolar lavage, chyle, chyme, cytosol, feces (in semi-fluid or fluid form), interstitial fluid, lymph, menses, mucus, pleural fluid, pus, saliva, sebum, semen, serum, sputum, sweat, synovial fluid, tears, urine and vitreous humor.

In one embodiment, the biological fluid is blood. In another embodiment, the acellular fraction of the blood is plasma.

As used herein, the term "infectious agent" refers to microorganisms that are generally unicellular, which can be multiplied and comprises: bacteria, fungi (yeasts or molds), viruses, and protozoans. The term "infectious agent" also refers to microorganisms that are pluricellular, which can be multiplied and comprises: worms and parasites.

Non-limiting examples of bacteria include Gram-positive or Gram-negative bacteria, mycobacteria or mollicutes.

Non-limiting examples of genus of Gram-negative bacteria of this invention include bacteria of the following genera: *Acetobacter, Morganella, Pseudomonas, Escherichia, Salmonella, Shigella, Enterobacter, Klebsiella, Serratia, Proteus, Campylobacter, Haemophilus, Vibrio, Yersinia, Stenotrophomonas, Brevundimonas, Ralstonia, Achromobacter, Fusobacterium, Prevotella, Branhamella, Neisseria, Burkholderia, Citrobacter, Hafnia, Edwardsiella, Aeromonas, Moraxella, Brucella, Pasteurella, Providencia,* and *Legionella.*

Non-limiting examples of genus of Gram-positive bacteria of this invention include bacteria of the following genera: *Enterococcus, Streptococcus, Staphylococcus, Bacillus, Paenibacillus, Lactobacillus, Listeria, Peptostreptococcus, Propionibacterium, Clostridium, Bacteroides, Gardnerella, Kocuria, Lactococcus, Leuconostoc, Micrococcus* and *Corynebacteria.*

Non-limiting examples of mycobacteria include but are not limited to, *Mycobacterium.*

Non-limiting examples of mollicutes include but are not limited to, *Mycoplasma* and *Ureaplasma.*

List of bacteria comprised within the list of infectious agents can be found in the LPSN website (list of prokaryotic names with standing nomenclatures: http://www.bacterio.net/index.html).

Non-limiting examples of viruses include but are not limited to members of the following families: Herpesviridae (e.g., varicella zoster virus, Epstein-Barr virus, herpes simplex virus), Adenoviridae, Poxviridae, Astroviridae, Bunyaviridae, Coronaviridae, Arteriviridae, Reoviridae (e.g., rotavirus), Parvoviridae (e.g., parvovirus B19), Picornaviridae (rhinovirus, coxsackievirus, enterovirus, hepatitis A virus), Bornaviridae, Filoviridae (e.g., Ebola virus, Marburg virus), Hepadnaviridae (e.g., hepatitis B), Hepeviridae (hepatitis E virus), Retroviridae (e.g., HIV, human T-lymphotropic virus), Orthomyxoviridae (e.g., influenza virus A, B, C), Togaviridae (e.g., rubella virus), Paramyxoviridae (e.g., respiratory syncytial virus, measles virus, mumps virus), Rhabdoviridae (e.g., rabies virus, bovine ephemeral fever virus, infectious hematopoietic necrosis virus, spring viraemia of carp virus, vesicular stomatitis indiana virus), Flavivirus (e.g., West Nile virus, dengue fever virus), Papillomaviridae, bacteriophage (e.g., Myoviridae, Podoviridae, Siphoviridae, Lipothrixviridae, Rudiviridae) Poxviridae (e.g., variola virus, cowpox virus).

Lists of viruses that can be considered as an infectious agent in the meaning of the present application can be found on the International Committee on the Taxonomy of Viruses (ICTV—http://www.ictvonline.org/virustaxonomy.asp).

Non-limiting examples of yeasts or molds include without limitation, *Candida, Cryptococcus, Nocardia, Penicillium, Alternaria, Rhodotorula, Aspergillus, Fusarium, Saccharomyces, Trichosporon, Pneumocystis.*

Non-limiting examples of protozoans include without limitation, *Trypanosoma* sp, *Babesia* sp, *Leishmania* sp, *Plasmodium* sp, *Wucheria* sp, *Toxoplasma* sp, *Cryptosporidium* sp.

Non-limiting examples of protozoans include without limitation *flagellates* (e.g., *Giardia, Trochomonas, Chilomastix, Enteromonas, Retortamoinas, Dientamoeba, Leishmania, Trypanosoma*), amoeboids (e.g., *Entamoeba, Acanthamoeba, Massisteria, Naegleria, Arcella, Amoeba, Chaos, Peloxyma, Syringammina*), sporozoans (e.g., *Plasmodium,* *Babesia, Cryptosporidium, Cyclospora, Isospora, Toxoplasma*), and ciliates (e.g., *Balantidium, Didinium, Colpoda, Stentor, Coleps, Paramecium, Vorticella, Tetrahymena, Cariocothrix*).

In one embodiment, the helminths are excluded from the methods of the invention.

In one embodiment, prion agents are excluded from the methods of the invention.

In one embodiment, the at least one detergent used in the methods of the invention comprises: non-ionic detergent and/or zwitterionic detergent and/or anionic detergent.

Said detergent acts without damaging the structure or the entirety of the infectious agent in order to preserve the nucleic acids of the infectious agent. The term "structure of the infectious agent" refers to complete viral particles, bacteria extracellular or intracellular bodies and the like.

In one embodiment, the detergent can be a non-ionic detergent, including without limitation, saponin, digitonin, Triton X-100, Triton X-100-R, Triton X-114, NP-40, Tween-20, Tween-40, Tween-80, Brij 98, Brij 58, Brij 35, Genapol C-100, Genapol X-100, Igepal, Brij 96/97, octyl β-D-glucopyranoside, and nonaethylene glycol monododecyl ether ($C_{12}E_9$) or a derivative thereof. In a preferred embodiment, the non-ionic detergent is saponin, Triton, NP-40, Tween or a derivative thereof.

The term "saponin" as used herein is a compound, usually a secondary metabolite, found in natural sources, in particular in various plants but also in marine species. Specifically, saponins are amphipathic glycosides grouped phenomenologically by the soap-like foaming they produce when shaken in aqueous solutions, and structurally by their composition of one or more hydrophilic glycoside moieties combined with a lipophilic triterpene derivative. The aglycone (glycoside-free portion) of a saponin is termed sapogenin. The number of saccharide-chains attached to the sapogenin/aglycone core can vary, as can the length of each chain. A typical chain length is from 1 to 11, with the numbers 2 to 5 being the most frequent, and with both linear and branched saccharide-chains being represented.

Monosaccharides such as D-glucose and D-galactose are among the most common components of the attached chains. The lipophilic aglycone can be any one of a wide variety of polycyclic organic structures originating from the serial addition of ten-carbon (C10) terpene units to compose a C30 triterpene skeleton, often with subsequent alteration to produce a C27 steroidal skeleton.

Derivative of saponin can include without limitation, triterpenoid saponin, saponin from *Saponaria* (*Quillaja saponaria*), from the family of Caryophyllaceae, from the family of Sapindaceae, from the families of Aceraceae (maples) and Hippocastanaceae, gypenosides saponin from *Gynostemma pentaphyllum* (*Gynostemma*, Cucurbitaceae), ginsenosides saponin (in *ginseng* or red *ginseng* (*Panax,* Araliaceae)), steroidal saponin also termed saraponin such as the diosgenin, tigogenin, sarsapogenin, cholestanol, furostanol and spirostanol saponins. Known furostanol steroid saponins are the saponins contained in fresh garlic, such as proto-isoeruboside-B and isoeruboside-B, while aged garlic extract contains also spirostanol steroid saponins. Other examples of spirostanol steroid saponins are the saponin from the underground parts of *Ruscus aculeatus,* from the rhizomes of *Tacca chantrieri,* from *Solanum hispidum,* from the tubers of *Dioscorea polygonoides,* from the harvested *Tribulus terrestris,* from *Lilium candidum.*

Steroid saponins are also the saponins contained in the root of the *Saponaria officinalis,* which were used as a soap before the advent of commercially manufactured soap, the saponins of *Yucca schidigera*, which grows in the arid Mexican desert country of Baja Calif., used by native American to make soap, the saponins contained in the soap lily, *Chlorogalum pomeridianum*, which were used as soap by native Americans, the saponins from the soapberry tree.

In one embodiment, the at least one detergent used in the methods of the invention is saponin from *saponaria* (*Quillaja saponaria*, also known as *Quillaja* bark, soap bark tree or soapbark).

In one embodiment, the at least one detergent used in the methods of the invention is a saponin with a sapogenin content of about 5% to about 50%, preferably from about 10% to about 40%, more preferably from about 20% to about 35%.

In one embodiment, the at least one detergent used in the methods of the invention is a saponin with a sapogenin content of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50%.

In one embodiment, the at least one detergent used in the methods of the invention is saponin from *saponaria* (*Quillaja saponaria*) with a sapogenin content of about 20-35%.

In another embodiment, the detergent can be a zwitterionic detergent that include without limitation, 3-[(3-cholamidopropyl)dimethylammonio]-1-propanesulfonate (CHAPS), 3-[(3-cholamidopropyl)dimethylammonio]-2-hydroxy-1-propanesulfonate (CHAPSO), amidosulfobetaine-14 (ASB-14), amidosulfobetaine-16 (ASB-16), sulfobetaine 3-10 (SB3-10), sulfobetaine 3-12 (SB3-12), and sulfobetaine 3-14 (SB3-14).

In another embodiment, the detergent can be an anionic detergent that include without limitation, sodium dodecyl sulfate, N-(alkyl $C_{10}$-$C_{16}$)—N,N-dimethylglycine betaine (EMPIGEN BB), lithium lauryl sulfate (LLS), sodium deoxycholate, sodium lauryl sulfate, cholesteryl hydrogen succinate, sodium deoxycholate, sodium taurocholate.

In one embodiment, the final concentration of the at least one detergent used in the methods of the invention is from about 0.01% w/v to about 10% w/v, from about 0.1% w/v to about 5% w/v, from about 0.1% w/v to about 1.5% w/v, from about 0.1% w/v to about 1% w/v, from about 0.1% w/v to about 0.5% w/v.

In one embodiment, the final concentration of the at least one detergent used in the methods of the invention is from about 0.1% w/v to about 4% w/v, from about 1% w/v to about 4% w/v.

In one embodiment, the detergent is preferably a non-ionic detergent, preferably saponin or a derivative thereof. In another embodiment, the at least one detergent used in the methods of the invention does not affect the structure of the infectious agent.

In another embodiment, the at least one nucleic acids-digesting enzyme used in the methods of the invention refers to enzymes that exhibit DNase and/or RNase activity.

Nucleic acids-digesting enzymes include, without limitation, nucleases such as for example deoxyribonuclease, ribonuclease, exonuclease, exodeoxyribonuclease, exoribonuclease, endonuclease, endodeoxyribonuclease, endoribonuclease.

Examples of nucleases include, but are not limited to, baseline-zero DNase, benzonase, DNase I, DNase II, endonuclease III, endonuclease IV, endonuclease V, endonuclease VIII, exonuclease I, exonuclease III, exonuclease V, exonuclease VII, exonuclease VIII, exonuclease T, lambda exonuclease, micrococcal nuclease, mung bean nuclease, nuclease BAL-31, nuclease P1, nuclease S1, T4 endonuclease V, T5 exonuclease, T7 endonuclease I, T7 exonuclease.

In one embodiment, the at least one nucleic acids-digesting enzyme used in the methods of the invention is selected from the group comprising, but not limited to, baseline-zero DNase and benzonase. In one embodiment, the nucleic acids-digesting enzymes used in the methods of the invention comprise or consist of baseline-zero DNase and benzonase.

In one embodiment, the concentration of the at least one nucleic acids-digesting enzyme is from about 0.1 units/µg to about 10 units/µg, preferably from about 0.5 units/µg to about 5 units/µg, more preferably about 1 unit/µg of protein.

In one embodiment, the acellular fraction of a biological fluid is contacted with at least one detergent and at least one nucleic acids-digesting enzyme for a period of time from about 5 minutes to about 5 hours, preferably from about 30 minutes to about 2 hours, more preferably about 1 hour.

In another embodiment, the acellular fraction of a biological fluid is contacted with at least one detergent and at least one nucleic acids-digesting enzyme for a period of time of about 5, 10, 15, 20, 30, 40, 45, 50 minutes, 1, 2, 3, 4 hours.

In another embodiment, the temperature of incubation is from about 30° C. to about 40° C., preferably 37° C. In another embodiment, the temperature of incubation is about 31, 32, 33, 34, 35, 36, 37, 38, 39° C.

In another embodiment, the acellular fraction of a biological fluid is contacted with at least one detergent for less than 30 minutes, 20 minutes, 10 minutes, then is contacted with the at least one nucleic acids-digesting enzyme for a period of time of about 5, 10, 15, 20, 30, 40, 45, 50 minutes, 1, 2, 3, 4 hours.

In one embodiment, the methods of the invention further comprise a step of inhibition of the nucleic acids-digesting enzyme activity.

Inhibiting nucleic acids-digesting enzymes is well known to the skilled artisan and can be performed using chelating agents or by heating the sample at a temperature ranging from about 60° C. to about 80° C., more preferably ranging from about 65° C. to about 80° C. In one embodiment, inhibition for nucleic acids-digesting enzymes can be performed by heating the sample at about 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C.

Inhibitors of nucleic acids-digesting enzymes are well known in the state of the art and include without limitation, ethylenediaminetetraacetic acid (EDTA), ethylene glycol tetraacetic acid (EGTA), dithiothreitol (DTT), β-mercaptoethanol, diethylpyrocarbonate (DEPC), and guanidine.

In one embodiment, the inhibition step is carried for at least about 5 minutes to about 20 minutes. In one embodiment, the inhibition step is carried for at least about 5, 6, 7, 8, 9, 10, 11, 12, 13, 14, 15, 16, 17, 18, 19, 20 minutes.

In one embodiment, the concentration of inhibitors of nucleic acids-digesting enzymes, such as for example EDTA, ranges from about 1 to about 10 mM. In one embodiment, the concentration of inhibitors of nucleic acids-digesting enzymes, such as for example EDTA, is about 1, 2, 3, 4, 5, 6, 7, 8, 9, 10 mM.

In one embodiment, the methods of the invention may further comprise an enrichment step for concentrating the infectious agent, such as for example centrifugation, ultra-centrifugation, salt precipitation or filtration steps. The skilled artisan will recognize which technique is the most efficient for such enrichment.

In one embodiment, the methods of the invention do not comprise a step of precipitation of the infectious agent using a precipitating agent such as polyethylene glycol (PEG), glycogen or nucleic acids.

In one embodiment, the methods of the invention may further comprise a step of preparation of homogenate of the infectious agent. Techniques to prepare homogenate are well known in the state of the art and include without limitation, mechanical homogenization (e.g., homogenizers, sonication), chemical homogenization (e.g., protease digestion).

In one embodiment, infectious agents are lysed under highly denaturing conditions at room temperature (15-25° C.). In one embodiment, infectious agents are lysed in the presence of proteinase K. In one embodiment, infectious agents are lysed in the presence of guanidinium chloride.

Treatment with chemicals and proteinase K is sufficient for complete lysis in the case of many Gram$^-$ bacteria, but the cell walls of Gram$^+$ bacteria and some Gram$^-$ bacteria must be disrupted by additional methods. For maximal lysis efficiency when working with difficult-to-lyse bacteria, mechanical and/or enzymatic homogenization can be additionally or alternatively carried out.

In one embodiment, the methods of the invention may further comprise a step for the infectious agents' nucleic acid extraction and the detection of said infectious agent.

In one embodiment, the methods of the invention detect a quantity of infectious agent inferior to about 10000 genome copies/mL, preferably inferior to about 1000 genome copies/mL, most preferably inferior to about 100 genome copies/mL.

The extraction/purification of nucleic acids is carried out by techniques well known to the skilled artisan. Such techniques include without limitation, phenol-chloroform extraction, alkaline extraction, guanidinium thiocyanate-phenol-chloroform extraction, binding on anion exchange resin, silica matrices, glass particle, diatomaceous earth, magnetic particles made from different synthetic polymers, biopolymers, porous glass or based on inorganic magnetic.

The extraction/purification of nucleic acids can be carried out using commercially available kits, such as QIAamp cador Pathogen Mini Kit (QIAGEN), QIAamp DNA Microbiome Kit (QIAGEN), DNeasy Blood & Tissue Kit (QIAGEN), QIAamp DNA Mini Kit (QIAGEN), QIAamp DSP DNA Mini Kit (QIAGEN), QIAamp DNA Blood Mini Kit (QIAGEN), QIAamp MinElute Virus Spin Kit Print (QIAGEN), PureLink Microbiome DNA Purification Kit (ThermoFisher Scientific), PureLink Viral RNA/DNA Mini Kit (ThermoFisher Scientific), MagMAX Pathogen RNA/DNA Kit (ThermoFisher Scientific), GeneJET Viral DNA/RNA Purification Kit (ThermoFisher Scientific), GenElute Bacterial Genomic DNA Kit (Sigma Aldrich), QuickExtract Bacterial DNA Extraction Kit (Illumina), ZR Fungal/Bacterial DNA MicroPrep Kit (Zymo Research), ZR Viral DNA Kit (Zymo Research).

In one embodiment, the methods of the invention may further comprise a step for the reverse transcription of extracted RNAs.

In some embodiment, the infectious agents may comprise RNA viruses. Such viruses have RNA as their genetic material. This nucleic acid is usually single-stranded RNA (ssRNA) but may be double-stranded RNA (dsRNA). Notable human diseases caused by RNA viruses include Ebola hemorrhagic fever, SARS, the common cold, influenza, hepatitis C, West Nile fever, polio and measles.

In one embodiment, in order to obtain near full-length genomic sequences derived from extracted viral RNA, it is first necessary to reverse-transcribe the extracted RNA to produce cDNA copies.

The reverse-transcription of RNAs is carried out by techniques well known to the skilled artisan, using a reverse transcriptase enzyme and a mix of 4 deoxyribonucleotides triphosphate (dNTPs), namely deoxyadenosine triphosphate (dATP), deoxycytidine triphosphate (dCTP), deoxyguanosine triphosphate (dGTP) and (deoxy)thymidine triphosphate (dTTP).

In one embodiment, the reverse-transcription of genomic RNA comprises a first step of first-strand cDNA synthesis. Methods for first-strand cDNA synthesis are well-known to the skilled artisan.

First-strand cDNA synthesis reactions can use a combination of sequence-specific primers, oligo(dT) or random primers. In one embodiment, the first-strand cDNA synthesis reaction uses sequence-specific primers. In one embodiment, the first-strand cDNA synthesis reaction uses random primers.

In one embodiment, a random primer used for first-strand cDNA synthesis comprises a fixed 5'-end sequence and a degenerate 3'-end sequence.

In one embodiment, a random primer used for first-strand cDNA synthesis comprises a fixed 3'-end sequence and a degenerate 5'-end sequence.

In one embodiment, the fixed sequence comprises from 20 to 40 nucleotides. In one embodiment, the fixed sequence comprises or consists of 20, 21, 22, 23, 24, 25, 26, 27, 28, 29, 30, 31, 32, 33, 34, 35, 36, 37, 38, 39, 40 nucleotides.

In one embodiment, the degenerate sequence comprises from 5 to 10 nucleotides. In one embodiment, the degenerate sequence comprises or consists of 5, 6, 7, 8, 9, 10 nucleotides.

As used herein, the term "degenerate sequence" refers to a sequence having a mixture of nucleotides, i.e., a mixture of A, T, C and/or G. In one embodiment, the degenerate sequence has a mixture of G and T (herein referred to as K). In one embodiment, the degenerate sequence has a mixture of C and T (herein referred to as Y).

In one embodiment, a random primer used for first-strand cDNA synthesis is Primer-$K_8$:

```
                                          (SEQ ID NO: 1)
       GTGAGTGATGGTTGAGGTAGTGTGGAGKKKKKKKK,
``` with K=T or G.

In one embodiment, a random primer used for first-strand cDNA synthesis is Primer-$K_9$:

```
                                          (SEQ ID NO: 3)
       GTGAGTGATGGTTGAGGTAGTGTGGAGKKKKKKKKK,
``` with K=T or G.

In one embodiment, a random primer used for first-strand cDNA synthesis is Primer-$K_{10}$:

```
                                          (SEQ ID NO: 4)
       GTGAGTGATGGTTGAGGTAGTGTGGAGKKKKKKKKKK,
``` with K=T or G.

In one embodiment, a random primer used for first-strand cDNA synthesis is Primer-K$_7$:

GTGAGTGATGGTTGAGGTAGTGTGGAGKKKKKKK, (SEQ ID NO: 5)

with K=T or G.

In one embodiment, a random primer used for first-strand cDNA synthesis is Primer-K$_6$:

GTGAGTGATGGTTGAGGTAGTGTGGAGKKKKKK, (SEQ ID NO: 6)

with K=T or G.

In one embodiment, a random primer used for first-strand cDNA synthesis is Primer-K$_5$:

GTGAGTGATGGTTGAGGTAGTGTGGAGKKKKK, (SEQ ID NO: 7)

with K=T or G.

In one embodiment, a random primer used for first-strand cDNA synthesis is Primer-Y$_8$:

CTCACTCATCCTTCACCTACTCTCCACYYYYYYYY, (SEQ ID NO: 8)

with Y=T or C.

In one embodiment, a random primer used for first-strand cDNA synthesis is Primer-Y$_9$:

CTCACTCATCCTTCACCTACTCTCCACYYYYYYYYY, (SEQ ID NO: 9)

with Y=T or C.

In one embodiment, a random primer used for first-strand cDNA synthesis is Primer-Y$_{10}$:

CTCACTCATCCTTCACCTACTCTCCACYYYYYYYYYY, (SEQ ID NO: 10)

with Y=T or C.

In one embodiment, a random primer used for first-strand cDNA synthesis is Primer-Y$_7$:

CTCACTCATCCTTCACCTACTCTCCACYYYYYYY, (SEQ ID NO: 11)

with Y=T or C.

In one embodiment, a random primer used for first-strand cDNA synthesis is Primer-Y$_6$:

CTCACTCATCCTTCACCTACTCTCCACYYYYYY, (SEQ ID NO: 12)

with Y=T or C.

In one embodiment, a random primer used for first-strand cDNA synthesis is Primer-Y$_5$:

CTCACTCATCCTTCACCTACTCTCCACYYYYY, (SEQ ID NO: 13)

with Y=T or C.

In one embodiment, the reverse-transcription of genomic RNA comprises a second step of second-strand cDNA synthesis. Methods for second-strand cDNA synthesis are well-known to the skilled artisan, and comprise, but are not limited to, hairpin-primed synthesis, Okayama and Berg procedure, Gubler and Hoffman procedure.

In one embodiment, the reverse-transcription of genomic RNA comprises a step of amplification of the first-strand cDNA. In one embodiment, the reverse-transcription of genomic RNA comprises a step of amplification of the second-strand cDNA.

The reverse-transcription of genomic RNA can be carried out using commercially available kits, such as SuperScript III First-Strand Synthesis System (ThermoFisher Scientific), SuperScript IV First-Strand Synthesis System (ThermoFisher Scientific), Transcriptor First Strand cDNA Synthesis Kit (Roche), First-Strand cDNA Synthesis Kit (GE Healthcare), ProtoScript First Strand cDNA Synthesis Kit (New England Biolabs).

The detection of the infectious agent may be carried out by techniques for amplifying and sequencing the nucleic acids of the infectious agent, for determining the cellular, physiological, phenotypic activity of the infectious agent. Preferably, the detection method used is a method for amplifying and sequencing the nucleic acids.

Techniques to amplify and sequence nucleic acids are well known to the skilled artisan. Techniques to amplify nucleic acid can include specific amplification methods as well as random amplification methods. Specific amplification techniques include but are not limited to, methods requiring temperature cycling (such as PCR, ligase chain reaction, transcription based amplification) and/or isothermal amplification systems (such as self-sustaining sequence replication, replicase system, helicase system, strand displacement amplification, rolling circle-based amplification and NASBA). In one embodiment, amplification of infectious agents' nucleic acids may be performed by polymerase chain reaction and/or any variations thereof, including, without limitation, allele-specific PCR, asymmetric PCR, hot-start PCR, intersequence-specific PCR, methylation-specific PCR, miniprimer PCR, multiplex ligation-dependent probe amplification, multiplex-PCR, nested PCR1 quantitative PCR, reverse transcription PCR and/or touchdown PCR. Amplification may be performed using primers and/or a collection of primers that may be selected from those capable of specific binding to nucleic acids of at least one infectious agent.

Random amplification techniques include without limitation, multiple displacement amplification (MDA), random PCR, random amplification of polymorphic DNA (RAPD) or multiple annealing and looping based amplification cycles (MALBAC).

DNA polymerases suitable to amplify nucleic acid comprise, but are not limited to, Taq polymerase Stoffel fragment, Taq polymerase, Advantage DNA polymerase, AmpliTaq, AmpliTaq Gold, Titanium Taq polymerase, KlenTaq DNA polymerase, Platinum Taq polymerase, Accuprime Taq polymerase, Pfu polymerase, Pfu polymerase turbo, Vent polymerase, Vent exo⁻ polymerase, Pwo polymerase, 9 Nm DNA polymerase, Therminator, Pfx DNA polymerase, Expand DNA polymerase, rTth DNA polymerase, DyNAzyme-EXT Polymerase, Klenow fragment, DNA polymerase I, T7 polymerase, Sequenase, Tfi polymerase, T4 DNA polymerase, Bst polymerase, Bca polymerase, phi-29 DNA polymerase and DNA polymerase Beta or modified versions thereof.

In one embodiment, amplification of the infectious agents' nucleic acids comprises a first step of looping. The utilization of primers set forth as SEQ ID NOs: 1 and 3 to 13 enables looping of amplicons which then prevents them from being further amplified in subsequent cycles, thus linearly amplifying the nucleic acids. The degenerate sequence of these primers anneals randomly to the genomic DNA molecule and/or cDNA molecule. After one extension, semi-amplicons are made, i.e., amplicon containing the fixed sequence on only the 5' end. During a second round of extension, semi-amplicons are used as a template, which results in a full-amplicon, i.e., an amplicon where the 3' end is complementary to the sequence on the 5' end.

In one embodiment, the looping step comprises from 4 to 10 extension cycles. In one embodiment, the looping step comprises or consists of 4, 5, 6, 7, 8, 9, 10 extension cycles. In a preferred embodiment, the looping step comprises or consists of 6 extension cycles.

In one embodiment, the looping step is carried out using a DNA polymerase. In one embodiment, the loop step is carried out using a Vent exo DNA polymerase.

In one embodiment, the sample is incubated at a temperature ranging from about 80° C. to about 100° C., for a period ranging from about 5 seconds to 5 minutes, prior to each extension cycle, preferably at about 94° C. for a period ranging from about 10 seconds to about 4 minutes.

In one embodiment, each extension cycle comprises several gradual heating steps. In one embodiment, each extension cycle comprises several gradual heating steps from about 4° C. to about 100° C., preferably from about 10° C. to about 65° C. In one embodiment, each extension cycle comprises gradual heating steps held for a period ranging from about 15 seconds to about 180 seconds, preferably from about 30 seconds to about 120 seconds, more preferably for about 45 seconds to about 120 seconds.

In one embodiment, amplification of the infectious agents' nucleic acids comprises a step of regular amplification. In one embodiment, amplification of the infectious agents' nucleic acids comprises a step of regular amplification by PCR. The utilization of a primer containing only a fixed sequence (SEQ ID NO: 2) enables to further amplified only full looped amplicons and to exponentially amplify the nucleic acids.

```
                                            (SEQ ID NO: 2)
GTGAGTGATGGTTGAGGTAGTGTGGAG.
```

In one embodiment, the step of regular amplification comprises from 15 to 30 extension cycles, preferably from 18 to 25 extension cycles, more preferably 21 extension cycles.

In one embodiment, the step of regular amplification is carried out using a DNA polymerase. In one embodiment, the step of regular amplification is carried out using a Vent exo⁻ DNA polymerase.

In one embodiment, amplified infectious agents' nucleic acids may be detected by hybridizing a probe and/or a collection of probes capable of specific binding to amplified nucleic acids of at least one infectious agent.

In one embodiment, the methods of the invention may further comprise a step for cleaning the nucleic acids.

Before preparing a nucleic acid library for sequencing, it can be desirable to remove single-strand primers and reaction products such as enzymes.

Techniques for nucleic acid clean-up are well known to the skilled artisan. In one embodiment, the step for cleaning the nucleic acids uses a single-strand-specific nuclease. Single-strand-specific nucleases include, but are not limited to, exonuclease I, mung bean nuclease, nuclease Bh1, nuclease P1, nuclease S1, BAL 31 nuclease. In one embodiment, the step for cleaning the nucleic acids uses exonuclease I. In one embodiment, the step for cleaning the nucleic acids comprises an incubation step at a temperature ranging from about 30 to about 45° C., preferably at about 37° C., for a period ranging from about 10 minutes to about 30 minutes, preferably for about 15 minutes.

In one embodiment, the step for cleaning the nucleic acids includes the dephosphorylation of phosphorylated ends of nucleic acids. In one embodiment, the dephosphorylation of nucleic acids uses an alkaline phosphatase, preferably shrimp alkaline phosphatase. In one embodiment, shrimp alkaline phosphatase can be completely and irreversibly inactivated by heating at a temperature ranging from about 60° C. to about 80° C., preferably at about 65° C., for a period ranging from about 10 minutes to about 30 minutes, preferably for about 15 minutes.

The step for cleaning the nucleic acids can be carried out using commercially available kits, such as illustra ExoProStar (GE Healthcare), GenUP Exo SAP Kit (BiotechRabbit).

In one embodiment, the methods of the invention may further comprise a step for sizing the nucleic acids.

Short-read sequencers, such as Illumina or Ion Torrent, operate best when fed DNA libraries that contain fragments of similar sizes, according to the manufacturer's recommendations. When libraries are not properly size-selected, these sequencers can become less efficient.

Techniques for DNA size selection are well known to the skilled artisan, including but not limited to, nucleic acid gel electrophoresis, bead-based protocols, pulsed-field gel electrophoresis (PFGE), automated size selection.

The step for sizing the nucleic acids can be carried out using commercially available kits, such as SPRIselect (Beckman Coulter), MagJET NGS Cleanup and Size Selection Kit (ThermoFisher Scientific), Select-a-Size DNA Clean & Concentrator (Zymo Research), NucleoMag NGS Clean-up and Size Select (Macherey-Nagel).

In one embodiment, the methods of the invention may further comprise a step for quantifying the amplified nucleic acids.

Techniques for quantifying amplified nucleic acids are well known to the skilled artisan, including but not limited to, UV absorption, intercalating dyes, 5' hydrolysis probes coupled with real-time quantitative PCR (qPCR), droplet digital emulsion PCRs.

The step for sizing the nucleic acids can be carried out using commercially available kits, such as Quant-iT dsDNA HS Assay Kit (ThermoFisher Scientific), Quant-iT dsDNA BR Assay Kit (ThermoFisher Scientific), Quant-iT PicoGreen dsDNA Assay Kit (ThermoFisher Scientific), SpectraMax Quant dsDNA Assay Kits (Molecular Devices), DNA Quantitation Kit (Sigma Aldrich), AccuClear Ultra High Sensitivity (Biotium), AccuBlue (Biotium), AccuGreen (Biotium).

Techniques for preparing nucleic acid sequencing libraries are well known to the skilled artisan.

The step for preparing nucleic acid sequencing libraries can be carried out using commercially available kits, such as Nextera XT DNA Library Prep Kit (Illumina), NEBNext DNA Library Prep Master Mix (New England Biolabs), NEBNext Ultra DNA Library Prep Kit (New England Biolabs), TruSeq Nano DNA Library Prep Kit (Illumina), JetSeq DNA Library Preparation Kit (Bioline).

In one embodiment, the detection of the nucleic acids may be carried out by random sequencing by high throughput sequencing (HTS) or next generation sequencing (NGS).

Methods for NGS of nucleic acid libraries are known to the skilled artisan, and comprise, but are not limited to, paired-end sequencing, sequencing by synthesis, single-read sequencing.

Platforms for NGS are available, and include, but are not limited to, Illumina MiSeq (Illumina), Ion Torrent PGM (ThermoFisher Scientific), PacBio RS (PacBio), Illumina GAIIx (Illumina), Illumina HiSeq 2000 (Illumina).

The step for sequencing nucleic acid libraries can be carried out using commercially available kits, such as MiSeq reagent kit v2 (Illumina).

In one embodiment, internal controls are used throughout the methods of the invention to assess the reliability of said methods.

In one embodiment, an internal control is added in the cellular fraction of a biological fluid. In one embodiment, an internal control is added in the acellular fraction of a biological fluid. In one embodiment, an internal control is added before, after or concomitantly with the at least one detergent. In one embodiment, an internal control is added before, after or concomitantly with the at least one nucleic acids-digesting enzyme. In one embodiment, an internal control is added before, after or concomitantly with the step of inhibition of the nucleic acids-digesting enzyme activity. In one embodiment, an internal control is added before, after or concomitantly with the enrichment step for concentrating the infectious agent. In one embodiment, an internal control is added before, after or concomitantly with the step of preparation of homogenate of the infectious agent. In one embodiment, an internal control is added before, after or concomitantly with the step of DNA or RNA extraction. In one embodiment, an internal control is added before, after or concomitantly with the step of amplification and sequencing of the nucleic acids of the infectious agent.

In one embodiment, the internal control is a nucleic acid sequence. In one embodiment, the internal control is a DNA sequence. In one embodiment, the internal control is an RNA sequence.

DNA sequences suitable as an internal control in the methods of the present invention comprise, but are not limited to, the genomic DNA and/or fragments thereof, of bacteriophages, such as bacteriophages from the Podoviridae, Myoviridae, Siphoviridae, Lipolhrixviridae, Rudiviridae, Ampullaviridae, Bicaudaviridae, Clavaviridae, Corticoviridae, Fuselloviridae, Globuloviridae, Guttaviridae, Inoviridae, Microviridae, Plasmaviridae, or Tectiviridae family.

DNA sequences suitable as an internal control in the methods of the present invention comprise, but are not limited to, the genomic DNA and/or fragments thereof, of bacteriophages, such as T1, T2, T3, T4, T5, T6, T7, M11, λ (Lambda), Φ (Phi), Φ29, P22, P37, μ (Mu), PBSX, P1Puna-like, P2, I3, Bcep 1, Bcep 43, Bcep 78, C2, L5, HK97, N15, *Acidianus filamentous* virus 1, *Sulfolobus islandicus* rod-shaped virus 1.

RNA sequences suitable as an internal control in the methods of the present invention comprise, but are not limited to, the genomic RNA and/or fragment thereof, of bacteriophages, such as bacteriophages from the Cystoviridae or Leviviridae family.

RNA sequences suitable as an internal control in the methods of the present invention comprise, but are not limited to, the genomic RNA and/or fragment thereof, of bacteriophages, such as MS2, Qβ.

In one embodiment, the internal control is a virus stock. In one embodiment, the internal control is a bacteriophage stock. In one embodiment, the internal control is a viral nanoparticle-encapsidated nucleic acid sequence.

Bacteriophages suitable as an internal control in the methods of the present invention comprise, but are not limited to, bacteriophages from the Podoviridae, Myoviridae, Siphoviridae, Lipothrixviridae, Rudiviridae, Ampullaviridae, Bicaudaviridae, Clavaviridae, Corticoviridae, Fuselloviridae, Globuloviridae, Guttaviridae, Inoviridae, Microviridae, Plasmaviridae, or Tectiviridae family.

Bacteriophages suitable as an internal control in the methods of the present invention comprise, but are not limited to, bacteriophage T3, T1, T2, T4.

In one embodiment, the internal control is a stock solution of bacteriophage T3. In one embodiment, the internal control is an extraction of genomic DNA derived from a stock solution of bacteriophage T3.

In one embodiment, the internal control is a stock solution of bacteriophage MS2. In one embodiment, the internal control is an extraction of genomic RNA derived from a stock solution of bacteriophage MS2.

Another object of the present invention is a kit-of-parts comprising at least one detergent and at least one nucleic acids-digesting enzyme.

In one embodiment, said kit comprises:
  a) at least one detergent,
  b) at least one nucleic acids-digesting enzyme,
  c) optionally, reagents, and
  d) optionally, instructions for use in a method according to the present invention.

By "kit" is intended any manufacture (e.g., a package or at least one container) comprising at least one detergent and at least one nucleic acids-digesting enzyme together (such as, for example, saponin and nucleases) or a container of at least one detergent and a container at least one nucleic acids-digesting enzyme. The kit may be promoted, distributed, or sold as a unit for performing the methods of the present invention. Furthermore, any or all of the kit reagents may be provided within containers that protect them from the external environment, such as in sealed and sterile containers. The kits may also contain a package insert describing the kit and methods for its use.

In one embodiment, the kit of the invention comprises:
  a) at least one detergent, selected from the group comprising, but not limited to, saponin, digitonin, Triton X-100, Triton X-100-R, Triton X-114, NP-40, Tween-20, Tween-40, Tween-80, Brij 98, Brij 58, Brij 35, Genapol C-100, Genapol X-100, Igepal, Brij 96/97, octyl β-D-glucopyranoside, and nonaethylene glycol monododecyl ether ($C_{12}E_9$) or a derivative thereof,
  b) at least one nucleic acids-digesting enzyme, selected from the group comprising, but not limited to, baseline-zero DNase, benzonase, DNase I, DNase II, endonuclease III, endonuclease IV, endonuclease V, endonuclease VIII, exonuclease I, exonuclease III, exonuclease V, exonuclease VII, exonuclease VIII, exonuclease T, lambda exonuclease, micrococcal nuclease, mung bean nuclease, nuclease BAL-31, nuclease P1, nuclease S1, T4 endonuclease V, T5 exonuclease, T7 endonuclease I, T7 exonuclease,
  c) optionally, reagents, selected from the group comprising, but not limited to, nucleic acid extraction reagents, reverse transcription reagents, nucleic acid amplification reagents, nucleic acid clean-up reagents, nucleic acid size-selection reagents, nucleic acid quantification reagents, nucleic acid library preparation reagents, nucleic acid library sequencing reagents, internal controls, and d) optionally, instructions for use in a method according to the present invention.

In one embodiment, the kit of the invention comprises:
a) at least one detergent, selected from the group comprising, but not limited to, saponin, Triton, NP-40, Tween or a derivative thereof,
b) at least one nucleic acids-digesting enzyme, selected from the group comprising, but not limited to, baseline-zero DNase, benzonase,
c) optionally, reagents, selected from the group comprising, but not limited to, nucleic acid extraction reagents, reverse transcription reagents, nucleic acid amplification reagents, nucleic acid clean-up reagents, nucleic acid size-selection reagents, nucleic acid quantification reagents, nucleic acid library preparation reagents, nucleic acid library sequencing reagents, internal controls, and
d) optionally, instructions for use in a method according to the present invention.

In one embodiment, the kit of the invention comprises:
a) saponin, preferably saponin 20-35% sapogenin,
b) baseline-zero DNase and/or benzonase nuclease,
c) optionally, reagents, selected from the group comprising, but not limited to, nucleic acid extraction reagents, reverse transcription reagents, nucleic acid amplification reagents, nucleic acid clean-up reagents, nucleic acid size-selection reagents, nucleic acid quantification reagents, nucleic acid library preparation reagents, nucleic acid library sequencing reagents, internal controls, and
d) optionally, instructions for use in a method according to the present invention.

In one embodiment, nucleic acid extraction reagents are selected from the group comprising, but not limited to, QIAamp Microbiome kit, QIAamp Cador Pathogen kit, linear polyacrylamide.

In one embodiment, reverse transcription reagents are selected from the group comprising, but not limited to, Superscript III first-strand synthesis system, primer oligonucleotides, dNTP. In one embodiment, primer oligonucleotides for reverse transcription are selected from the group comprising, but not limited to, primers with nucleic acid sequences set forth as SEQ ID NOs: 1 and 3-13.

In one embodiment, nucleic acid amplification reagents are selected from the group comprising, but not limited to, Vent exo⁻ DNA polymerase, primer oligonucleotides, Thermopol buffer, dNTPs. In one embodiment, primer oligonucleotides for nucleic acid amplification are selected from the group comprising, but not limited to, primers with nucleic acid sequences set forth as SEQ ID NOs: 1-13.

In one embodiment, nucleic acid clean-up reagents are selected from the group comprising, but not limited to, exonuclease I, exonuclease I buffer.

In one embodiment, nucleic acid size-selection reagents are selected from the group comprising, but not limited to, SPRIselect reagent kit.

In one embodiment, nucleic acid quantification reagents are selected from the group comprising, but not limited to, Quant-iT dsDNA HS assay kit, Quant-iT dsDNA BR assay kit.

In one embodiment, nucleic acid library preparation reagents are selected from the group comprising, but not limited to, Nextera XT DNA Library Preparation kit.

In one embodiment, nucleic acid library sequencing reagents are selected from the group comprising, but not limited to, MiSeq reagent kit v2.

In one embodiment, internal controls are selected from the group comprising, but not limited to, stock solution of bacteriophage T3, extraction of genomic DNA derived from a stock solution of bacteriophage T3, stock solution of bacteriophage MS2, extraction of genomic RNA derived from a stock solution of bacteriophage MS2. In one embodiment, al controls are selected from the group comprising, but not limited to, a stock solution of bacteriophage T3 and/or an extraction of genomic RNA derived from a stock solution of bacteriophage MS2.

EXAMPLES

The present invention is further illustrated by, but is by no means limited to, the following examples. Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Example 1: Decrease of HNA Concentration in Acellular Fractions Issued from Plasma Samples An acellular fraction obtained from the supernatant of blood centrifuged at 1600 rpm (300 g) for 10 minutes, then further centrifuged at 13000 rpm (15000 g) for 10 minutes (to ensure full elimination of vesicles or aggregates), was treated with nucleases (conditions: 1 hour at 37° C.) in the absence or in presence of 0.01% to 1% w/v saponin (Table 1).

Resulting HNA concentrations was tested by a highly sensitive Alu repetitive sequence qPCR. Incubation of the acellular fraction in presence of saponin was efficient in the range 0.01-1%. An optimal concentration of 0.3 to 1% saponin plus nucleases divided the amount of HNA compared to only nucleases (i.e., the nuclease-resistant fraction) by a factor of at least 18 in this experiment. In fact, much higher HNA load reduction (up to 25 ct, i.e., more than $10^6$) can also be demonstrated for acellular fraction richer in HNA, as the treatment by saponin plus nucleases routinely decreases the HNA concentration down to background levels represented by the mix of qPCR.

TABLE 1

| Material EAH-040 | Condition | Crossing Point (CP) | Ratio treated/non-treated* | Ratio treated with (nuclease + saponin)/ (nuclease only)* |
|---|---|---|---|---|
| Plasma clarified by high speed centrifugation | Non-treated | 16.17 16.28 | | |
| | Nucleases only | 22.74 22.74 | 91.4 | |
| | Nucleases + Saponin 20-35 0.01% | 23.27 23.44 | 140 | 1.5 |
| | Nucleases + Saponin 20-35 0.03% | 24.65 24.76 | 357 | 3.9 |
| | Nucleases + Saponin 20-35 0.1% | 24.81 24.92 | 398 | 4.3 |
| | Nucleases + Saponin 20-35 0.3% | 26.85 26.95 | 1634 | 17.9 |
| | Nucleases + Saponin 20-35 0.1% | 27.04 26.83 | 1675 | 18.31 |
| Mix only | Non-treated | 27.41 27.24 | | |

*all the calculations were done assuming a PCR efficacy = 2.

In conclusion, we show that saponin increases the accessibility to nucleic acids-digesting enzymes like nucleases of free (non-cell associated) HNA in acellular fractions like plasma samples.

Example 2: Whole-Genome Next Generation Sequencing (NGS) of Infectious Agents in Biological Samples (in this Case nHNA=Microbe NA (MNA))

New tools for infectious agents (bacteria, viruses, fungi, protozoans) detection directly from biological samples are emerging: they include random sequencing of biological samples by high throughput sequencing (HTS). The main obstacle to the identification of infectious agents in biological samples is the extreme small quantity of MNAs present, in combination with a relatively high level of HNA. In the initial developments of the techniques, all nucleic acids from the samples were extracted and random-amplified by random polymerase chain reaction (PCR), RCA (rolling circle amplification), MDA (multiple displacement amplification). The drawback of this methodology is the simultaneous amplification of both MNA and HNA. This limits the sensitivity of downstream MNAs detection: for example, detection with microarrays loses sensitivity, and HTS needs deeper sequencing to reach adequate levels of sensitivity. Even if single molecule sequencing is to be used, increasing the ratio MNA to HNA is pivotal to increase the sensitivity for a given number of reads. To bypass this drawback, hydrolysis of host DNA by nucleases has been proposed.

We show here a relative increase of infectious agents (virus and bacteria) reads from infectious agents spiked in plasma. The readout was the proportion of reads targeted to the infectious agents to the number of reads to HNA. Treatment by nucleases is very strongly improved in the presence of saponin in the range 0.1 to 1%. Saponin at these concentrations preserves MNA within viral and/or bacterial structures while giving access to HNA previously not accessible to nucleases.

Efficacy for the Detection of Viruses in Plasma Samples by NGS: Experiment 1

In this experiment, blood samples were spiked with three viruses: two DNA viruses (VZV and B19) and one RNA virus (rotavirus). Plasma samples were then obtained following routine procedures in biomedical laboratories, by pelleting blood cells at 1600 rpm (300 g) for 10 minutes. The supernatants, named "acellular fractions", were further centrifuged at 13000 rpm (15000 g) to totally ensure lack of blood cells in the resulting supernatant, named "viral fraction". This viral fraction was treated with saponin 0.3% w/v plus nucleases, random-amplified and sequenced on the Proton sequencer (Life Technology).

The results show a strong (4.1 to 6.4) enhancement of the number of reads for the viral targets. In parallel, the proportion of human reads was reduced (×0.68) (Table 2). This leads to a ratio virus/human reads increased by 7.1-fold in the presence of saponin, meaning that a lower depth of sequencing would be necessary to get the same number of reads against the viral targets.

TABLE 2

| | | # reads normalized for 2.5M reads (coverage (%)) | | | |
|---|---|---|---|---|---|
| Material | Condition | Varicella Zoster virus | Rotavirus A | Parvovirus B19 | Human |
| S15-0026-01-3 | Nucleases | 1209 (31.3) | 246 (36.8) | 114 (53.52) | 2312500 |
| S15-0026-02-3 | Nucleases + Saponin 20-35 0.3% | 6539 (22.4) | 1568 (53.6) | 472 (29.61) | 1585000 |
| | Ratio saponin/no saponin | 5.4 | 6.4 | 4.1 | 0.68 |

TABLE 2-continued

| | | # reads normalized for 2.5M reads (coverage (%)) | | | |
|---|---|---|---|---|---|
| Material | Condition | Varicella Zoster virus | Rotavirus A | Parvovirus B19 | Human |
| | Ratio total virus/human Nucleases: 0.07% Nucleases + Saponin: 0.5% Relative ratios w/wo saponin: 7.1 | | | | |

Efficacy for the Detection of Viruses in Plasma Samples by NGS: Experiment 2

In this experiment, a plasma sample obtained by routine procedures in biomedical laboratories obtained from a donor (id: 076) was spiked with three DNA viruses (VZV, feline herpesvirus, canine parvovirus) and two RNA viruses (rotavirus, feline calicivirus). The plasma was further centrifuged at 13000 rpm (15000 g) and the supernatant (or "viral fraction") was treated with saponin 1% w/v plus nucleases, random-amplified and sequenced on the Proton sequencer (Life Technology).

The results show a strong (1.3 to 19.2) enhancement of the number of reads for the viral targets. In parallel, the proportion of human reads was reduced (×0.50) (Table 3). This leads to a ratio virus/human reads increased by 13.6-fold in the presence of saponin, meaning that a lower depth of sequencing would be necessary to get the same number of reads against the viral targets.

Efficacy for the Detection of Bacteria in Plasma Samples

In this experiment, blood samples were spiked with Gram$^-$ bacteria (*Acinetobacter baumannii, Morganella morganii*) and Gram$^+$ bacteria (*Enterococcus faecalis, Streptococcus agalactiae*). Plasma samples were then obtained following procedures used routinely in biomedical laboratories, by pelleting blood cells at 1600 rpm (300 g). The supernatants (or "acellular fractions") were further centrifuged at 13000 rpm (15000 g) for 10 minutes to pellet bacteria from plasma. This pellet, also named herein as "bacterial fraction", was treated with or without saponin 1% w/v plus nucleases, random-amplified and sequenced on the Proton sequencer (Life Technology).

The results show a strong (21.5 to 43.5) enhancement of the number of reads from the bacterial targets. In parallel, the proportion of human reads was strongly reduced (×0.80) (Table 4). This leads to a ratio bacteria/human reads increased by 112-fold in the presence of saponin. Genome coverage (i.e., the fraction of the bacterial genome sequenced) was 1.3-7.8% in absence of saponin and 32.2-82.3% in presence of saponin.

TABLE 3

| | | # reads normalized for 10M reads | | | | | |
|---|---|---|---|---|---|---|---|
| Material STP 19 | Condition | Feline herpesvirus | Varicella zoster virus | Feline calicivirus | Canine parvovirus 2 | Rotavirus A | Human |
| S-14-0118-03 | Nucleases | 75607 | 18317 | 148 | 306 | 189180 | 4644353 |
| S-14-0118-04 | Nucleases + Saponin 20-35 1% | 1450498 | 237195 | 1505 | 982 | 250329 | 2338926 |
| | Ratio saponin/ no saponin | 19.18 | 12.95 | 10.17 | 3.21 | 1.32 | 0.50 |
| | Ratio total virus/ human Nucleases: 6.1% Nucleases + Saponin: 82.9% Relative ratios w/wo saponin: 13.6 | | | | | | |

TABLE 4

| | | # reads normalized for 2.5M reads (coverage (%)) | | | | |
|---|---|---|---|---|---|---|
| Material | Condition | A. baumannii | M. morganii | E. faecalis | S. agalactiae | Human |
| S-15-0024-04-2 | Nucleases | 430 (1.3) | 510 (1.5) | 384 (1.6) | 1728 (7.8) | 2422500 |
| S-15-0024-03-2 | Nucleases + Saponin 20-35 1% | 25029 (35.2) | 19447 (32.2) | 50623 (67.5) | 165816 (82.3) | 1930000 |
| | Ratio saponin/ no saponin | 58 (27) | 38.5 (21.5) | 131.8 (42.2) | 95 (10.6) | 0.80 |
| | Ratio total bacteria/ human Nucleases: 0.12% | | | | | |

TABLE 4-continued

| | | # reads normalized for 2.5M reads (coverage (%)) | | | | |
|---|---|---|---|---|---|---|
| Material | Condition | A. baumannii | M. morganii | E. faecalis | S. agalactiae | Human |
| | Nucleases + Saponin: 13.5% Relative ratios w/wo saponin: 112 | | | | | |

Thus, a privileged sequence of steps is:
1) treatment of an acellular fraction with saponin and nucleases to digest HNAs,
2) inactivation of the nuclease,
3) extraction of NAs from the acellular fraction,
4) readout that might be PCR, NGS following random amplification or NGS on single molecules, hybridization on DNA arrays.

Example 3: Viral Nucleic Acids Isolation, Amplification, Library Construction and Sequencing Based on the experiments described herein above, a complete and standardized protocol for the detection of viruses in plasma samples was developed.
Extraction 1 µL of bacteriophage T3 stock was extemporaneously diluted in PBS to a final concentration of $10^5$ bacteriophage genome copies/mL. At the same time, 1 mL of a freshly mixed blood sample was transferred in a 1.5 mL microtube, and centrifuged for 10 minutes at 300 g at room temperature.

297 µL of plasma (i.e., the supernatant phase) was transferred into a 1.5 mL microtube, and supplemented with 3 µL of T3 bacteriophage diluted at $10^5$ genome copies/mL. The sample was further centrifuged for 10 minutes at 12000 g at room temperature, and 150 µL of supernatant was transferred into a new 1.5 mL microtube. The residual supernatant was discarded.

A 10% w/v of saponin solution was prepared by dissolving 0.1 g of saponin (Saponin 20-35% sapogenin from Sigma-Aldrich, Ref.: S4521) in 1 mL of ultrapure DNase- and RNase-free distilled water (ThermoFisher Scientific, Ref.: 10977035). 4 µL of Benzonase nuclease (VWR, Ref.: 70664-3), 4 µL of Baseline-ZERO DNase (Tebu-Bio, Ref.: DB0711K), 18 µL of Baseline-ZERO DNase buffer and 1.8 µL of 10% w/v of saponin were added (without premixing the enzymes). After shaking and pulse-spinning, the sample was left for incubation at 37° C. for 1 hour.

The sample was then pulse-spined, and 20 µL of 30 mM EDTA pH 8.0 (Sigma Aldrich, Ref.: 03690) were added. The tube was then left for 10 minutes at 65° C. in a heating-block or water bath to inactivate the nucleases.

The nucleic acid extraction per se was carried out using the QIAamp Cador Pathogen mini-kit (QIAGEN, Ref.: 54104), following the manufacturer's instructions.

Briefly, 20 µL of Proteinase K, then 100 µL of "VXL" buffer (25-50% guanidinium chloride, 2.5-10% Triton-X) containing 10 µg of linear polyacrylamide (98 µL of "VXL" buffer+2 µL of linear polyacrylamide (Life Technologies, Ref.: AM9520) at 5 mg/mL) were added. The sample was mixed by pulse-vortexing, and left for incubation at room temperature (20-25° C.) for 15 minutes.

350 µL of "ACB" buffer (30-50% guanidinium thiocyanate, isopropanol) were then added and the sample was mixed by pulse-vortexing.

The lysate was loaded onto a QIAamp Mini column set on a collecting tube, centrifuged for 1 minute at 6000 g, and the flow through was discarded. The column was set on a new collecting tube, washed by adding 600 µL of "AW1" buffer (50-70% guanidinium chloride, ethanol), and centrifuged for 1 minute at 6000 g. The flow through was discarded, the column set on a new collecting tube, washed by adding 600 µL of "AW2" buffer (70% ethanol), and centrifuged for 1 minute at 6000 g. The flow through was discarded, the column set on a new collecting tube, and centrifuged for 2 minutes at 12000 g to dry the membrane. The flow through was discarded and the column set on a new 1.5 mL RNase and DNase-free tube. 50 µL of "AVE" buffer (RNase-free water, 0.04% sodium azide) were added to the center of the membrane, incubated for 1 to 2 minutes on the bench, then centrifuged for 1 minute at 12000 g. The column was finally discarded.

1 µL of a MS2 bacteriophage RNA solution was added to the recovered eluate. The sample was placed on ice or at +4° C. for immediate use. Otherwise, it should be stored at −20° C. (for up to one month) or −80° C. (for up to five years).
Successive Tags for Library Amplification (STLA)

Within the population of extracted nucleic acids, a possibility exists that some viral RNAs are present. It is therefore essential to first proceed with a reverse transcription to convert these RNAs into cDNAs. The first-strand cDNA synthesis can be performed with the SuperScript III First-Strand Synthesis System (Life Technologies, Ref.: 18080-051) and a single primer containing a fixed 5'-end sequence (from 25 bp to 35 bp) and 8 consecutives G/T nucleotides at the 3'-end. In the present experiment, a "Primer-$K_8$" (with K=G or T) was used (SEQ ID NO: 1).

4 µL of the nucleic acids sample previously recovered were transferred in a 0.2 mL RNase- and DNase-free microtube, and supplemented with 1 µL of a mix containing 0.5 µL of 10 mM of each dNTPs (New England Biolabs, Ref.: N04475) and 0.5 µL of 20 µM Primer-$K_8$ oligonucleotide (SEQ ID NO: 1). After mixing, the sample was heated at 75° C. for 5 minutes, then cooled down to for 2 minutes at 25° C.

5 µL of a mix were added to the sample, containing:
1 µL of 10× SuperScript III RTion Buffer,
2 µL of 25 mM $MgCl_2$,
1 µL of 100 mM DTT,
0.5 µL of 40 U/µL RNAseOUT,
0.5 µL of 200 U/µL SuperScript III RTAse.

The 0.2 mL microtube was placed in a thermocycler, and incubated 10 minutes at 25° C. for annealing and elongation of primers, then 60 minutes at 45° C., for first-strand cDNA synthesis. The recovered nucleic acids were immediately used, or stored at −20° C. for later use.

The successive tags for library amplification (STLA) method uses the Vent exo⁻ DNA polymerase. A single primer is used (Primer-$K_8$, already used for reverse transcription (SEQ ID NO: 1)) for 6 random amplification cycles. From the second cycle, every priming on already tagged fragments will lead to a panhandle-like structure harboring the adapter sequence (namely, the Primer-$K_8$ sequence, set forth as SEQ ID NO: 1) at both extremities. The Vent exo⁻ DNA polymerase is used for this procedure. Before starting, all buffers are carefully vortexed before use.

To the 10 µL of sample obtained previously (4 µL of the nucleic acids+1 µL of a dNTP/primer mix+5 µL of SuperScript III RTion mix), were added 19.5 µL of a mix containing:

3 µL of 10× Thermopol buffer,
3 µL of 10 mM $MgSO_4$,
1.2 µL of 5 mM each dNTPs,
12.3 µL of ultrapure DNase/RNase-free distilled water.

After mixing, the sample was incubated for 3 minutes at 95° C., then quickly placed on ice for 2 minutes. The sample was then pulse-spined and supplemented with 0.5 µL (2 U/µL) of Vent exo⁻ DNA polymerase (New England Biolabs, Ref: M0257S). The sample was then mixed and incubated in a thermocycler:

45 seconds at 10° C.,
45 seconds at 20° C.,
45 seconds at 30° C.,
45 seconds at 40° C.,
45 seconds at 50° C.,
2 minutes at 65° C.,
20 seconds at 94° C.

This program was repeated 5 times (6 cycles altogether), and finally hold at +4° C. Nucleic acids were then immediately used or stored at −20° C. for later utilization.

The amplification step is performed using a primer (SEQ ID NO: 2), corresponding to the fixed part of the primer used during the first-strand cDNA synthesis, the modification consisting of the deletion of the 3'-end random sequence. This step exponentially amplifies the panhandle-like structures. The Vent exo⁻ DNA polymerase is used for this procedure. Before starting, all buffers are carefully vortexed before use.

To the 30 µL of sample obtained previously, were added 30 µL of a mix containing:

3 µL of 10× Thermopol buffer,
3 µL of 10 mM $MgSO_4$,
3 µL of 10 µM primer (SEQ ID NO: 2),
1.2 µL of 5 mM each dNTPs,
14 of 2 U/µL Vent exo⁻ DNA polymerase,
18.8 µL of ultrapure DNase/RNase-free distilled water.

The sample was then mixed and incubated in a thermocycler:

| | |
|---|---|
| Cycle 1 | 3 minutes at 95° C., 30 seconds at 65° C., 1 minute at 72° C., |
| Cycles 2-21 | 20 seconds at 95° C., 30 seconds at 65° C., 1 minute at 72° C. |

Nucleic acids were then kept at +4° C. if used within a week, or at −20° C. for longer periods.

Sample Cleaning Before Sequencing Library Construction

Before sequencing library construction, the sample should be cleaned to remove single-strand primers and reaction products.

Removal of single-strand primers can be performed using the exonuclease I in order to degrade the single-strand primer oligonucleotides from the previous reactions mixtures.

After PCR completion, the sample was pulse-spined, supplemented with 6.7 µL of 10× Exonuclease I buffer and 1 µL of Exonuclease I (New England Biolabs, Ref.: M0293S), and incubated for 15 minutes at 37° C.

To further purify the amplified nucleic acids, two successive size selection steps using SPRI beads (SPRIselect reagent kit, Beckman Coulter, Ref.: B23317) can be performed. The two ratios successively used were 0.8× and 0.6×.

Firstly, a SPRI beads suspension was vortexed until it appeared homogeneous in color. 65 µL of nucleic acids previously obtained were transferred in a 1.5 mL LoBind tube (Dominique Dutscher, Ref.: 033871) with 52 µL of SPRI beads suspension. The total reaction volume was mixes by pipetting 10 times, and incubated for 1 minute at room temperature. The tube was placed in a magnetic rack for 3 minutes, or until the solution was clear. The supernatant was then removed and discarded.

Leaving the tube on the magnet, 180 µL of freshly prepared 85% ethanol were added to the sample and incubated for 30 seconds. The ethanol supernatant was then removed and discarded without disturbing the pellet. To remove residual ethanol, the tube was pulse-spined, placed back in the magnetic rack, and the supernatant was carefully removed with a 20 µL pipettor, without disturbing the pellet.

Keeping the tube on the magnet, the beads were air-dried at room temperature for no more than 1 minute. The tube was then removed from the magnetic rack, and 50 µL of nuclease-free water were added to the sample. The mixture was pipetted up and down 5 times, and vortexed for 10 seconds to mix thoroughly.

The tube was further pulse-spined and placed back in the magnetic rack for at least 1 minute. After the solution cleared, the supernatant, containing the eluted DNA, was transferred to a new 1.5 mL LoBind tube without disturbing the pellet.

Secondly, to the 50 µL of sample previously recovered, 30 µL of SPRI beads suspension were added. The total reaction volume was mixes by pipetting 10 times, and incubated for 1 minute at room temperature. The tube was placed in a magnetic rack for 3 minutes, or until the solution was clear. The supernatant was then removed and discarded.

Leaving the tube on the magnet, 180 µL of freshly prepared 85% ethanol were added to the sample and incubated for 30 seconds. The ethanol supernatant was then removed and discarded without disturbing the pellet. To remove residual ethanol, the tube was pulse-spined, placed back in the magnetic rack, and the supernatant was carefully removed with a 20 µL pipettor, without disturbing the pellet.

Keeping the tube on the magnet, the beads were air-dried at room temperature for no more than 1 minute. The tube was then removed from the magnetic rack, and 20 µL of nuclease-free water were added to the sample. The mixture was pipetted up and down 5 times, and vortexed for 10 seconds to mix thoroughly.

The tube was further pulse-spined and placed back in the magnetic rack for at least 1 minute. After the solution cleared, the supernatant, containing the eluted DNA, was transferred to a new 1.5 mL LoBind tube without disturbing the pellet.

Quantification of Amplified DNAs

200 µL of Quant-iT dsDNA HS/BR working solution were prepared by mixing 1 µL of Quant-iT dsDNA HS/BR reagent and 199 µL of Quant-iT dsDNA HS/BR buffer (1:200 dilution) (Quant-iT dsDNA HS/BR assay kit, ThermoFisher Scientific, Ref.: Q32851/Q32853).

To 10 µL of each of the two bacteriophage λ DNA standard provided with the kit, 190 µL of Quant-iT dsDNA HS/BR working solution were added and the tubes were allowed to incubate at room temperature for 2 minutes.

To 5 μL of amplified DNA sample previously recovered, and diluted twice, 195 μL of Quant-iT dsDNA HS/BR working solution were added and the tube was allowed to incubate at room temperature for 2 minutes.

Using the Qubit 2.0 fluorimeter (ThermoFisher Scientific, Ref.: Q32866), the calibration program was run with the two standards, by selecting "DNA", then "dsDNA HS/BR".

Finally, the nucleic acid sample was read. The value given by the Qubit 2.0 fluorimeter corresponds to the concentration of the diluted sample in the assay tube. This value should be corrected by the dilution factor to obtain the concentration of the amplified DNAs after the cleaning steps.

The amplified nucleic acids can now be used for the construction of the sequencing library for NGS sequencing.

Sequencing Library Construction and Running

This step requires 1 ng of input DNA and can be performed using the Nextera XT DNA Library Preparation kit (Illumina, Ref.: FC-131-1096) following the manufacturer's instructions (Document #15031942 v01, January 2016).

The library quantification is performed on the 2100 Bio-Analyzer device (Agilent technologies, Ref.: G2939AA) without baseline subtraction. Obtained libraries are compatible with the MiSeq sequencing system (Illumina).

These libraries are then processed on a 150 bases single-read sequencing run using an Illumina MiSeq system and the MiSeq regent kit v2 (Illumina, Ref: MS-102-2002), following the manufacturer's instructions.

Finally, the obtained sequences, or "sequencing reads", can be aligned against a databank, preferably a multiple pathogen databank containing the genomes of infectious agents of clinical importance.

Example 4: Bacterial Nucleic Acids Isolation, Amplification, Library Construction and Sequencing Based on the experiments described herein above, a complete and standardized protocol for the detection of bacteria in plasma samples was developed.

Extraction

The nucleic acid extraction per se was carried out using the QIAamp DNA Microbiome kit (QIAGEN, Ref: 51704), following the manufacturer's instructions.

Briefly, 300 μL of a freshly mixed blood sample was transferred in a 2 mL microtube, supplemented with 700 μL of PBS to adjust the volume to 1 mL, and with 500 μL of "AHL" buffer (3-10% saponin, 10-20% sucrose), then incubated for 30 minutes at room temperature with end-over-end rotation, or, alternatively, in a thermomixer at 600 rpm.

The sample was then centrifuged at 10000 g for 10 minutes at room temperature, and the supernatant was discarded.

A 10% w/v of saponin solution was prepared by dissolving 0.1 g of saponin (Saponin 20-35% sapogenin from Sigma-Aldrich, Ref.: S4521) in 1 mL of ultrapure DNase- and RNase-free distilled water (ThermoFisher Scientific, Ref.: 10977035). The recovered pellet was resuspended with 184.2 μL of "RDD" buffer (QIAGEN proprietary composition), and supplemented with 2.5 μL of Benzonase nuclease (VWR, Ref.: 70664-3) and 5.8 μL of 10% w/v of saponin (without premixing the enzymes). After shaking and pulse-spinning, the sample was left for incubation at 37° C. for 30 minutes on a thermomixer at 600 rpm.

20 μL of Proteinase K were further added and the sample was left for incubation at 56° C. for 30 minutes, on a thermomixer at 600 rpm.

After a brief spinning of the tube to remove condensation, 200 μL of "ATL" buffer (1-3% sodium dodecyl sulfate—SDS), containing reagent DX (antifoaming reagent) were added (1490 μL of "ATL" buffer+10 μL of reagent DX).

The entire volume of the sample was then transferred into a Pathogen Lysis Tube L (provided with the kit) containing glass beads. The tube was placed on a Vortex adapter for microtubes and vortexed at full speed for 10 minutes in order to lyse bacteria. The tube was further centrifuged at 10000 g for 1 minute to reduce the amount of foam after lysis.

198 μL of supernatant were transferred into a 1.5 mL microtube. At the same time, 1 μL of bacteriophage T3 stock was extemporaneously diluted in PBS to a final concentration of $10^6$ bacteriophage genome copies/mL. 2 μL of this working solution were added to the sample.

40 μL of Proteinase K were further added and the sample was vortexed and left for incubation at 56° C. for 30 minutes, on a thermomixer at 600 rpm. 200 μL of "APL2" buffer (30-50% guanidinium thiocyanate) were then added. The sample was mixed by pulse-vortexing for 30 seconds and incubated at 70° C. for 10 minutes.

200 μL of ethanol were then added and the sample was mixed by pulse-vortexing for 15-30 seconds, before loading the lysate onto a QIAamp UCP Mini column (provided with the kit), set on a collecting tube. The column was centrifuged for 1 minute at 6000 g, and the flow through was discarded. The column was set on a new collecting tube, washed by adding 500 μL of "AW1" buffer (50-70% guanidinium chloride, ethanol), and centrifuged for 1 minute at 6000 g. The flow through was discarded, the column set on a new collecting tube, washed by adding 500 μL of "AW2" buffer (70% ethanol), and centrifuged for 3 minutes at 12000 g. The flow through was discarded, the column set on a new collecting tube, and centrifuged for 1 extra minute at 12000 g to dry the membrane. The flow through was discarded and the column set on a new 1.5 mL RNase and DNase-free tube.

50 μL of "AVE" buffer (RNase-free water, 0.04% sodium azide) were added to the center of the membrane, incubated for 5 minutes on the bench, then centrifuged for 1 minute at 6000 g. The column was finally discarded.

The sample was placed on ice or at +4° C. for immediate use. Otherwise, it should be stored at −20° C. (for up to one month) or −80° C. (for up to five years).

Successive Tags for Library Amplification (STLA)

The successive tags for library amplification (STLA) method uses the Vent exo⁻ DNA polymerase. A single primer is used (Primer-$K_8$, already used for reverse transcription (SEQ ID NO: 1)) for 6 random amplification cycles. From the second cycle, every priming on already tagged fragments will lead to a panhandle-like structure harboring the adapter sequence at both extremities. The Vent exo⁻ DNA polymerase is used for this procedure. Before starting, all buffers are carefully vortexed before use.

4 μL of sample obtained previously were transferred in a 0.2 mL RNase and DNase-free tube, and supplemented with 25.5 μL of a mix containing:
  3 μL of 10× Thermopol buffer,
  3 μL of 10 mM $MgSO_4$,
  1.2 μL of 5 mM each dNTPs,
  0.5 μL of 20 μM Primer-$K_8$ oligonucleotide (SEQ ID NO: 1),
  17.8 μL of ultrapure DNase/RNase-free distilled water.

After mixing, the sample was incubated for 3 minutes at 95° C., then quickly placed on ice for 2 minutes. The sample was then pulse-spined and supplemented with 0.5 μL (2 U/μL) of Vent exo⁻ DNA polymerase (New England Biolabs, Ref.: M0257S). The sample was then mixed and incubated in a thermocycler:

45 seconds at 10° C.,
45 seconds at 20° C.,
45 seconds at 30° C.,
45 seconds at 40° C.,
45 seconds at 50° C.,
2 minutes at 65° C.,
20 seconds at 94° C.

This program was repeated 5 times (6 cycles altogether), and finally hold at +4° C. Nucleic acids were then immediately used or stored at −20° C. for later utilization.

The amplification step is performed using a primer (SEQ ID NO: 2), corresponding to the fixed part of the primer used during the first-strand cDNA synthesis, the modification consisting of the deletion of the 3'-end random sequence. This step exponentially amplifies the panhandle-like structures. The Vent exo⁻ DNA polymerase is used for this procedure. Before starting, all buffers are carefully vortexed before use.

To the 30 μL of sample obtained previously, were added 30 μL of a mix containing:

3 μL of 10× Thermopol buffer,
3 μL of 10 mM MgSO₄,
3 μL of 10 μM primer (SEQ ID NO: 2),
1.2 μL of 5 mM each dNTPs,
1 μL of 2 U/μL Vent exo⁻ DNA polymerase,
18.8 μL of ultrapure DNase/RNase-free distilled water.

The sample was then mixed and incubated in a thermocycler:

| | |
|---|---|
| Cycle 1 | 3 minutes at 95° C., 30 seconds at 65° C., 1 minute at 72° C., |
| Cycles 2-21 | 20 seconds at 95° C., 30 seconds at 65° C., 1 minute at 72° C. |

Nucleic acids were then kept at +4° C. if used within a week, or at −20° C. for longer periods.

Sample Cleaning Before Sequencing Library Construction

Before sequencing library construction, the sample should be cleaned to remove single-strand primers and reaction products.

Removal of single-strand primers can be performed using the exonuclease I in order to degrade the single-strand primer oligonucleotides from the previous reactions mixtures.

After PCR completion, the sample was pulse-spined, supplemented with 6.7 μL of 10× Exonuclease I buffer and 1 μL of Exonuclease I (New England Biolabs, Ref.: M0293S), and incubated for 15 minutes at 37° C.

To further purify the amplified nucleic acids, two successive size selection steps using SPRI beads (SPRIselect reagent kit, Beckman Coulter, Ref.: B23317) can be performed. The two ratios successively used were 0.8× and 0.6×.

Firstly, a SPRI beads suspension was vortexed until it appeared homogeneous in color. 65 μL of nucleic acids previously obtained were transferred in a 1.5 mL LoBind tube (Dominique Dutscher, Ref.: 033871) with 52 μL of SPRI beads suspension. The total reaction volume was mixes by pipetting 10 times, and incubated for 1 minute at room temperature. The tube was placed in a magnetic rack for 3 minutes, or until the solution was clear. The supernatant was then removed and discarded.

Leaving the tube on the magnet, 180 μL of freshly prepared 85% ethanol were added to the sample and incubated for 30 seconds. The ethanol supernatant was then removed and discarded without disturbing the pellet. To remove residual ethanol, the tube was pulse-spined, placed back in the magnetic rack, and the supernatant was carefully removed with a 20 μL pipettor, without disturbing the pellet.

Keeping the tube on the magnet, the beads were air-dried at room temperature for no more than 1 minute. The tube was then removed from the magnetic rack, and 50 μL of nuclease-free water were added to the sample. The mixture was pipetted up and down 5 times, and vortexed for 10 seconds to mix thoroughly.

The tube was further pulse-spined and placed back in the magnetic rack for at least 1 minute. After the solution cleared, the supernatant, containing the eluted DNA, was transferred to a new 1.5 mL LoBind tube without disturbing the pellet.

Secondly, to the 50 μL of sample previously recovered, 30 μL of SPRI beads suspension were added. The total reaction volume was mixes by pipetting 10 times, and incubated for 1 minute at room temperature. The tube was placed in a magnetic rack for 3 minutes, or until the solution was clear. The supernatant was then removed and discarded.

Leaving the tube on the magnet, 180 μL of freshly prepared 85% ethanol were added to the sample and incubated for 30 seconds. The ethanol supernatant was then removed and discarded without disturbing the pellet. To remove residual ethanol, the tube was pulse-spined, placed back in the magnetic rack, and the supernatant was carefully removed with a 20 μL pipettor, without disturbing the pellet.

Keeping the tube on the magnet, the beads were air-dried at room temperature for no more than 1 minute. The tube was then removed from the magnetic rack, and 20 μL of nuclease-free water were added to the sample. The mixture was pipetted up and down 5 times, and vortexed for 10 seconds to mix thoroughly.

The tube was further pulse-spined and placed back in the magnetic rack for at least 1 minute. After the solution cleared, the supernatant, containing the eluted DNA, was transferred to a new 1.5 mL LoBind tube without disturbing the pellet.

Quantification of Amplified DNAs

200 μL of Quant-iT dsDNA HS/BR working solution were prepared by mixing 1 μL of Quant-iT dsDNA HS/BR reagent and 199 μL of Quant-iT dsDNA HS/BR buffer (1:200 dilution) (Quant-iT dsDNA HS/BR assay kit, ThermoFisher Scientific, Ref.: Q32851/Q32853).

To 10 μL of each of the two bacteriophage λ DNA standard provided with the kit, 190 μL of Quant-iT dsDNA HS/BR working solution were added and the tubes were allowed to incubate at room temperature for 2 minutes.

To 5 μL of amplified DNA sample previously recovered, and diluted twice, 195 μL of Quant-iT dsDNA HS/BR working solution were added and the tube was allowed to incubate at room temperature for 2 minutes.

Using the Qubit 2.0 fluorimeter (ThermoFisher Scientific, Ref.: Q32866), the calibration program was run with the two standards, by selecting "DNA", then "dsDNA HS/BR".

Finally, the nucleic acid sample was read. The value given by the Qubit 2.0 fluorimeter corresponds to the concentration of the diluted sample in the assay tube. This value should be corrected by the dilution factor to obtain the concentration of the amplified DNAs after the cleaning steps.

The amplified nucleic acids can now be used for the construction of the sequencing library for NGS sequencing.

Sequencing Library Construction and Running

This step requires 1 ng of input DNA and can be performed using the Nextera XT DNA Library Preparation kit (Illumina, Ref.: FC-131-1096) following the manufacturer's instructions (Document #15031942 v01, January 2016).

The library quantification is performed on the 2100 Bio-Analyzer device (Agilent technologies, Ref.: G2939AA) without baseline subtraction. Obtained libraries are compatible with the MiSeq sequencing system (Illumina).

These libraries are then processed on a 150 bases single-read sequencing run using an Illumina MiSeq system and the MiSeq regent kit v2 (Illumina, Ref.: MS-102-2002), following the manufacturer's instructions.

Finally, the obtained sequences, or "sequencing reads", can be aligned against a databank, preferably a multiple pathogen databank containing the genomes of infectious agents of clinical importance.

Example 5: Analytical Performance Characteristics

In this experiment, blood samples were spiked with nine infectious agents (Table 5).

TABLE 5

| Infectious agent | Type | Concentration (gc/mL) |
|---|---|---|
| Varicella Zoster virus (VZV) | Double strand DNA virus | $10^4$ |
| BK polyomavirus | Circular double strand DNA virus | $10^4$ |
| Parainfluenza-3 virus | Single strand RNA virus | $10^4$ |
| Rotavirus A | Segmented double strand RNA virus | $10^3$ |
| Parvovirus B19 | Single strand DNA virus | $2.5 \times 10^3$ |
| Klebsiella pneumoniae | Gram$^-$ bacteria | $10^4$ |
| Staphylococcus aureus | Gram$^+$ bacteria | $10^4$ |
| Enterococcus faecalis | Gram$^+$ bacteria | $10^4$ |
| Enterococcus faecium | Gram$^+$ bacteria | $10^4$ | gc/mL: genome copies/mL

Limits of Detection

The limits of detection (LoD) for the nine infectious agents were determined from 8 independent blood samples, of which 5 were repeated (starting from the nucleic acid extracts), meaning 13 samples all together.

Amongst the five viruses, three were detected in all situations (13/13): VZV, Parvovirus B19 and rotavirus A. The BK polyomavirus was detected in all but one duplicate of the 5 samples processed twice (12/13 positives).

Spiked at the concentration of $10^4$ gc/mL, the Parainfluenza-3 virus was detected with only few tens to hundreds sequencing reads in several samples, while undetected in other samples. This data means that the spiking concentration for the Parainfluenza-3 virus corresponds to the extreme limit of the LoD.

The LoD calculated for the viruses are thus:

| VZV | $10^4$ gc/mL, |
|---|---|
| Rotavirus A | $10^3$ gc/mL, |
| Parvovirus B19 | $2.5 \times 10^3$ gc/mL, |
| BK polyomavirus | $10^4$ gc/mL, |
| Parainfluenza-3 virus | $10^4$ gc/mL. |

Amongst the three Gram' bacteria, *Enterococcus faecalis* was detected in all situations (13/13) and *Enterococcus faecium* and *Staphylococcus aureus* in 12 out of 13 samples.

These last two bacteria were detected with a moderate confidence in the 13$^{th}$ sample, indicating that all of the above-mentioned Gram$^+$ bacteria spiked at $10^4$ gc/mL are readily detectable at this concentration.

The Gram$^-$ bacteria *Klebsiella pneumoniae* spiked at $10^4$ gc/mL was detected in all 13 samples, with high confidence in 9 cases, and low in the remaining 4 cases. In no sample *Klebsiella pneumoniae* went undetected.

The LoD calculated for the bacteria are thus:

| *Enterococcus faecalis* | $10^4$ gc/mL, |
|---|---|
| *Enterococcus faecium* | $10^4$ gc/mL, |
| *Staphylococcus aureus* | $10^4$ gc/mL, |
| *Klebsiella pneumoniae* | $10^4$ gc/mL. |

Repeatability

Repeatability was assessed at two different levels: by testing identical NGS libraries loaded onto different Illumina MiSeq flowcells, and analyzed independently. This approach allows to assess variability introduced by the NGS sequencing stochastic step on the data output.

Two different NGS libraries were loaded onto two NGS runs. Amongst the 18 conditions (nine infectious agents and two different libraries), only 1 condition gave a different result. For two replicates of the same library, the rotavirus A was undetected or detected with a moderate confidence. More importantly, when an infectious agent was detected in a given point of a sample, it was also detected in the duplicate, indicating a consistent repeatability for detected agents.

Then, experiments starting from the same viral and bacterial extracts but processed independently up to the NGS sequencing were performed. This was used to monitor the variability introduced by the nucleic acid amplification, the NGS library construction and sequencing steps.

Such type of experiment was performed on five different blood samples, each giving a viral and a bacterial extract. For each viral and bacterial extracts, a duplicate of nucleic acid amplification, NGS library construction and sequencing onto two different MiSeq flowcells was performed. The analysis was performed on ten NGS libraries issued from five blood samples.

Out of the 45 duplicates (nine infectious agents spiked into five different blood samples), only 7 were discordant. Regarding the detection, the 7 cases can be classified as follows:

From positive to moderate confidence level:
4 cases (2× Parainfluenza-3 virus; *Enterococcus faecium; Staphylococcus aureus*),
From positive to negative detection:
1 case (BK polyomavirus),
From positive to low confidence level:
1 case (*Klebsiella pneumoniae*),
From low confidence level to negative level:
1 case (*Klebsiella pneumoniae*).

Amongst the 7 discordant cases, the parainfluenza-3 virus and the *Klebsiella pneumoniae*, agents showing the less reproducible data, represent 4 cases. More importantly, the extreme variation represented by a positive detection and a non-detection within a single duplicate is only found in a single case out of the 45 studied.

Altogether, this data indicates a very good repeatability for the detection of infectious agents starting from a single nucleic acid extract.

Example 6: Internal Controls

Internal Control 1

During the preparation of the viral fractions and bacterial fractions, a first internal control, herein termed "internal control 1", is used to assess the reliability of the methods of the invention. Internal control 1 is an ultrapure stock solution of bacteriophage T3.

In the viral fraction, internal control 1 is spiked in the plasma, prior to saponin and nuclease treatment, and serves to monitor all the subsequent steps of the procedure.

In the bacterial fraction, internal control 1 is added after the saponin and nuclease treatment, but prior to the extraction of bacterial DNA. It is used to monitor the bacterial DNA purification and the subsequent steps of the procedure.

The differences between the viral and bacterial fractions preparation have an implication on the monitoring of these procedures by the addition of internal control 1. Indeed, extraction of viral nucleic acids from viral particles is achieved by a "soft" treatment (typically, using chaotropic salts), as compared to the strong mechanical lysis required to break-down bacterial cell walls, especially for Gram+ bacteria. Such a hard treatment would inevitably degrade the nucleic acid of internal control 1 and prevent further monitoring of the procedure. Consequently, the addition of internal control 1 in the bacterial fraction is performed right after the mechanical lysis and prior the purification of bacterial nucleic acids.

Internal Control 2

During the preparation of the viral fractions, a second internal control, herein termed "internal control 2", may be used to assess the reliability of the methods of the invention. Internal control 2 is an extraction of genomic RNA derived from an ultrapure stock solution of bacteriophage MS2.

In the viral fraction, internal control 2 may be added in the viral nucleic acids extract, right after the purification of viral nucleic acids. In this case, it is used to monitor a reverse transcription step, required for the detection and sequencing of RNA viruses, as well as the subsequent steps of the procedure together with internal control 1.

The methods of the invention are deemed to be reliable if enough sequencing reads for internal controls 1 and 2 are recovered, i.e., more than about 10% of the genome covered.

The invention claimed is:

1. A method for isolating, amplifying, and sequencing viral nucleic acids from a biological fluid comprising:
   a) centrifuging the biological fluid under conditions suitable for ensuring the elimination of cells, vesicles and aggregates in the resulting supernatant, and recovering said supernatant, thereby obtaining a viral fraction of said biological fluid,
   b) contacting the viral fraction of the biological fluid with at least one detergent and at least one nucleic acids-digesting enzyme,
   c) inactivating the at least one nucleic acids-digesting enzyme,
   d) extracting viral nucleic acids,
   e) optionally, reverse-transcribing viral genomic RNAs,
   f) amplifying viral genomic DNA and/or, where viral genomic RNAs were reverse-transcribed at step e), viral cDNA, and
   g) sequencing amplified viral genomic DNA and/or, where viral genomic RNAs were reverse-transcribed at step e), amplified viral cDNA.

2. The method according to claim 1, wherein the sequencing of said infectious agents' nucleic acids is carried out by high throughput sequencing.

3. The method according to claim 1, wherein the at least one detergent is selected from the group consisting of non-ionic detergent, zwitterionic detergent, and anionic detergent.

4. The method according to claim 1, wherein the at least one detergent is selected from the group consisting of saponin, Triton, NP-40, Tween and derivative detergents thereof.

5. The method according to claim 1, wherein the at least one detergent is saponin with a sapogenin content of about 5% to about 50%.

6. The method according to claim 1, wherein the at least one nucleic acids-digesting enzyme is a nuclease having DNase and/or RNase activity.

7. The method according to claim 1, wherein the at least one detergent is saponin with a final concentration ranging from 0.1% w/v to 1% w/v.

8. The method according to claim 1, wherein the at least one detergent is saponin with a sapogenin content of about 20% to about 35%.

9. The method according to claim 1, wherein centrifuging the biological fluid at step a) comprises at least one step of centrifugation under conditions suitable for the full elimination of vesicles or aggregates in the biological fluid.

10. The method according to claim 1, wherein centrifuging the biological fluid at step a) comprises at least one step of centrifugation at a relative centrifugal force of between 12 000 g and 15 000 g.

* * * * *